(12) United States Patent
Schrul et al.

(10) Patent No.: US 11,273,265 B2
(45) Date of Patent: Mar. 15, 2022

(54) EXTERNAL CAP HAVING NEEDLE PROTECTION CAP REMOVER ELEMENT AND METHOD FOR ASSEMBLING AN INJECTION DEVICE

(71) Applicant: Ypsomed AG, Burgdorf (CH)

(72) Inventors: Christian Schrul, Burgdorf (CH); Markus Tschirren, Burgdorf (CH); Markus Hunziker, Gelterkinden (CH)

(73) Assignee: Ypsomed AG, Burgdorf (CH)

( * ) Notice: Subject to any disclaimer, the term of this patent is extended or adjusted under 35 U.S.C. 154(b) by 273 days.

(21) Appl. No.: 16/259,524

(22) Filed: Jan. 28, 2019

(65) Prior Publication Data
US 2019/0151564 A1    May 23, 2019

Related U.S. Application Data

(63) Continuation of application No. PCT/CH2017/000062, filed on Jun. 21, 2017.

(30) Foreign Application Priority Data

Jul. 28, 2016    (CH) .................................. 00989/16

(51) Int. Cl.
*A61M 5/32*    (2006.01)
*A61M 5/20*    (2006.01)

(52) U.S. Cl.
CPC ........ *A61M 5/3204* (2013.01); *A61M 5/3202* (2013.01); *A61M 5/326* (2013.01);
(Continued)

(58) Field of Classification Search
CPC .............. A61M 5/3204; A61M 5/3202; A61M 5/3213; A61M 2005/3215
See application file for complete search history.

(56) References Cited

U.S. PATENT DOCUMENTS 5,843,036 A    12/1998  Olive et al.
5,928,205 A     7/1999  Marshall
(Continued)

FOREIGN PATENT DOCUMENTS

AU    2002346711 A8    6/2003
AU    2008285447 B2    4/2013
(Continued)

*Primary Examiner* — Jason E Flick
*Assistant Examiner* — Anna E Goldberg-Richmeier
(74) *Attorney, Agent, or Firm* — Dorsey & Whitney LLP

(57) ABSTRACT

An injection device includes a product container having an injection needle, a needle protection cap detachably secured to the product container surrounds the injection needle and seals same in a sterile manner. A cap is connected to the needle protection cap, via a remover element having an engaging element, in such a way that the removal of the cap from the injection device brings about the removal of the needle protection cap from the product container, where the engaging element is in an engaging position in relation to the needle protection cap, where in the engaging position, a section of the needle protection cap is arranged distally in line with the engaging element, characterized in that the cap and the engaging element are coupled in such a way that the cap is or can be moved relative to the engaging element during the removal from the injection device.

10 Claims, 15 Drawing Sheets

(52) U.S. Cl.
CPC ..... *A61M 5/2033* (2013.01); *A61M 2005/208* (2013.01); *A61M 2005/3247* (2013.01); *A61M 2005/3267* (2013.01); *A61M 2205/273* (2013.01); *A61M 2205/581* (2013.01)

(56) References Cited

U.S. PATENT DOCUMENTS

| | | | |
|---|---|---|---|
| 7,771,397 | B1 | 8/2010 | Olson |
| 10,022,503 | B2 | 7/2018 | Julian et al. |
| 10,092,706 | B2 | 10/2018 | Denzer et al. |
| 10,118,001 | B2 | 11/2018 | Fourt et al. |
| 10,159,805 | B2 | 12/2018 | Schoonmaker |
| 10,159,806 | B2 | 12/2018 | Björk et al. |
| 10,179,214 | B2 | 1/2019 | Llewellyn-hyde et al. |
| 10,188,802 | B2 * | 1/2019 | Hodgson ............ A61M 5/3257 |
| 10,207,059 | B2 | 2/2019 | Perche et al. |
| 10,881,799 | B2 | 1/2021 | Hirschel et al. |
| 2003/0181859 | A1 | 9/2003 | Brunel |
| 2007/0173772 | A1 | 7/2007 | Liversidge |
| 2008/0228147 | A1 | 9/2008 | David-Hegerich et al. |
| 2008/0312602 | A1 | 12/2008 | Barrow-Williams et al. |
| 2009/0054849 | A1 | 2/2009 | Burnell et al. |
| 2009/0105661 | A1 | 4/2009 | Chevallier et al. |
| 2009/0182284 | A1 | 7/2009 | Morgan |
| 2009/0234297 | A1 | 9/2009 | Jennings |
| 2010/0016793 | A1 | 1/2010 | Jennings et al. |
| 2010/0094214 | A1 | 4/2010 | Abry et al. |
| 2010/0185178 | A1 | 7/2010 | Sharp et al. |
| 2010/0286619 | A1 | 11/2010 | Abry |
| 2010/0286620 | A1 | 11/2010 | Edginton et al. |
| 2011/0034878 | A1 | 2/2011 | Radmer et al. |
| 2011/0054411 | A1 | 3/2011 | Dowds et al. |
| 2012/0029439 | A1 | 2/2012 | Hudson et al. |
| 2012/0031904 | A1 | 2/2012 | Kuhn et al. |
| 2012/0035542 | A1 | 2/2012 | Pongprairochana |
| 2012/0130342 | A1 | 5/2012 | Cleathero |
| 2012/0186075 | A1 | 7/2012 | Edginton |
| 2012/0191046 | A1 | 7/2012 | Larsen et al. |
| 2012/0191048 | A1 | 7/2012 | Eaton |
| 2012/0232491 | A1 | 9/2012 | Jennings |
| 2013/0079718 | A1 | 3/2013 | Shang et al. |
| 2013/0116625 | A1 | 5/2013 | Holmqvist |
| 2013/0131602 | A1 | 5/2013 | Kemp et al. |
| 2013/0144219 | A1 | 6/2013 | Evans et al. |
| 2013/0190693 | A1 | 7/2013 | Ekman et al. |
| 2013/0204197 | A1 | 8/2013 | Bicknell et al. |
| 2013/0256166 | A1 | 10/2013 | Perot et al. |
| 2013/0310746 | A1 | 11/2013 | Wozencroft |
| 2013/0331796 | A1 | 12/2013 | Wozencroft |
| 2014/0221936 | A1 | 8/2014 | Edhouse et al. |
| 2014/0243753 | A1 * | 8/2014 | Bostrom ............ A61M 5/3213 604/198 |
| 2014/0343503 | A1 | 11/2014 | Holmqvist |
| 2014/0343504 | A1 | 11/2014 | Bicknell et al. |
| 2014/0343507 | A1 | 11/2014 | Karlsson et al. |
| 2014/0364812 | A1 | 12/2014 | Lumme et al. |
| 2014/0371684 | A1 | 12/2014 | Holmqvist |
| 2015/0258284 | A1 | 9/2015 | Fenster et al. |
| 2015/0273151 | A1 | 10/2015 | Mcloughlin et al. |
| 2016/0106929 | A1 | 4/2016 | Fournier et al. |
| 2016/0144129 | A1 | 5/2016 | Mosebach et al. |
| 2016/0144132 | A1 | 5/2016 | Scanlon |
| 2016/0175539 | A1 | 6/2016 | Riedel et al. |
| 2016/0206831 | A1 | 7/2016 | Darras et al. |
| 2016/0287810 | A1 | 10/2016 | Keim et al. |
| 2016/0296713 | A1 | 10/2016 | Schader et al. |
| 2016/0325044 | A1 | 11/2016 | Tschirren et al. |
| 2016/0354550 | A1 | 12/2016 | Ward et al. |
| 2016/0354551 | A1 | 12/2016 | Keim et al. |
| 2016/0354552 | A1 | 12/2016 | Keim et al. |
| 2016/0375199 | A1 | 12/2016 | Ward et al. |
| 2017/0080153 | A1 | 3/2017 | Maxfield |
| 2017/0274151 | A1 | 9/2017 | Allen |
| 2017/0354789 | A1 | 12/2017 | Bendek |
| 2017/0354790 | A1 | 12/2017 | Atterbury et al. |
| 2017/0361030 | A1 | 12/2017 | Moore |
| 2018/0001025 | A1 | 1/2018 | Sarkinen et al. |
| 2018/0028762 | A1 | 2/2018 | Maxfield |
| 2018/0133407 | A1 | 5/2018 | Kemp et al. |
| 2018/0169349 | A1 | 6/2018 | Mosebach et al. |
| 2018/0185589 | A1 | 7/2018 | Kemp et al. |
| 2018/0200446 | A1 | 7/2018 | Grimoldby et al. |
| 2018/0200453 | A1 | 7/2018 | Wendland et al. |
| 2018/0228984 | A1 | 8/2018 | Sall |
| 2018/0289899 | A1 | 10/2018 | Gould |
| 2018/0296764 | A1 | 10/2018 | Davies et al. |
| 2018/0296768 | A1 | 10/2018 | Gould et al. |
| 2018/0311442 | A1 | 11/2018 | Saussaye et al. |

FOREIGN PATENT DOCUMENTS

| | | |
|---|---|---|
| AU | 2008285450 B2 | 4/2013 |
| CN | 108025144 A | 5/2018 |
| CN | 109310823 A | 2/2019 |
| DE | 202011109359 U1 | 3/2012 |
| EP | 3416707 A1 | 12/2018 |
| GB | 2465389 A | 5/2010 |
| WO | 2009081133 A1 | 7/2009 |
| WO | 2012082818 A2 | 6/2012 |
| WO | 2017198589 A1 | 11/2017 |
| WO | 2018011417 A1 | 1/2018 |

* cited by examiner

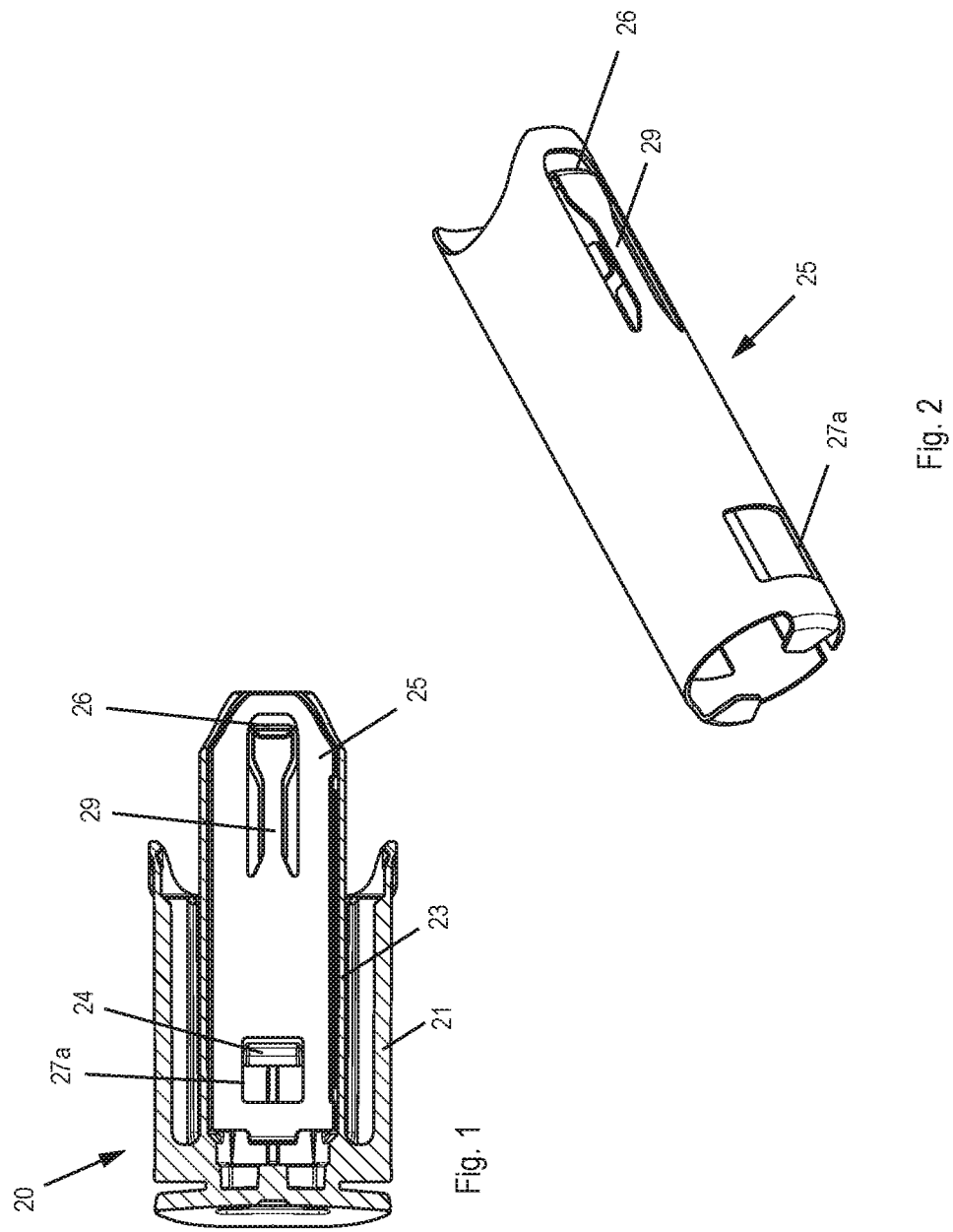

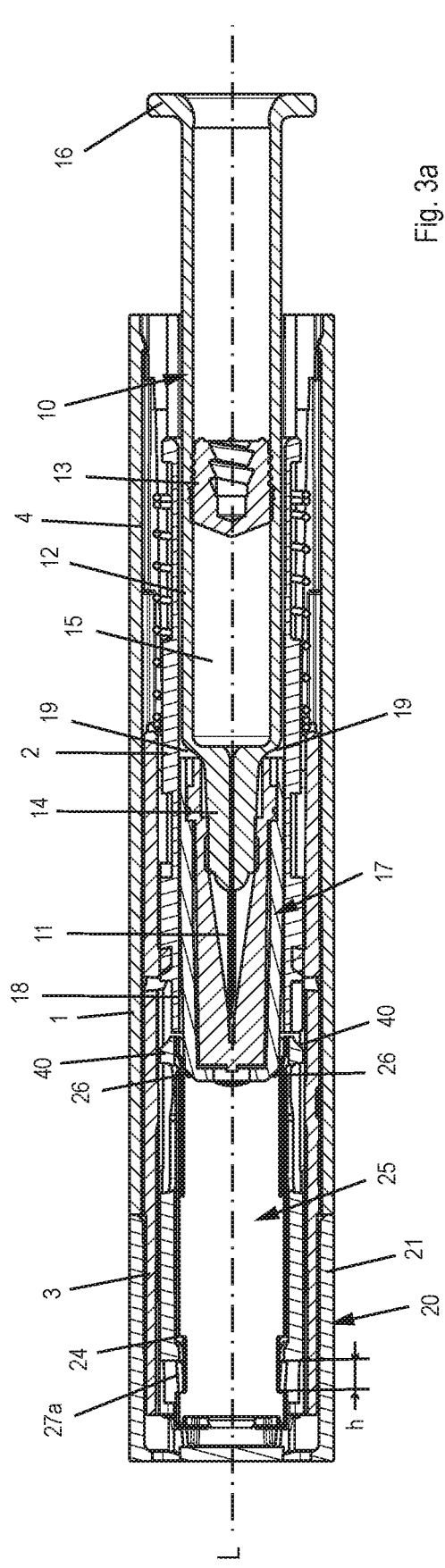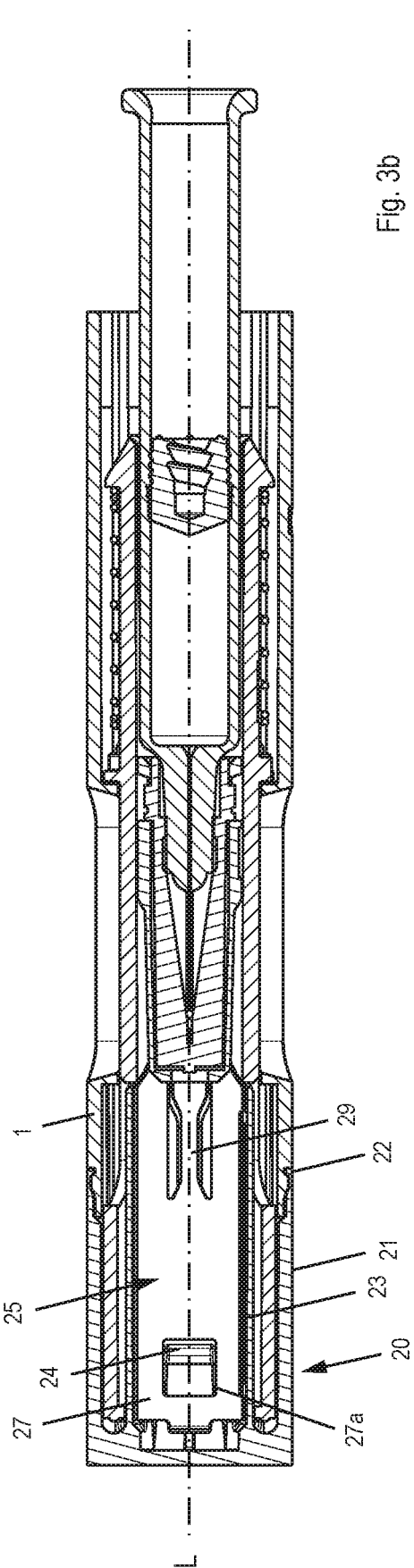

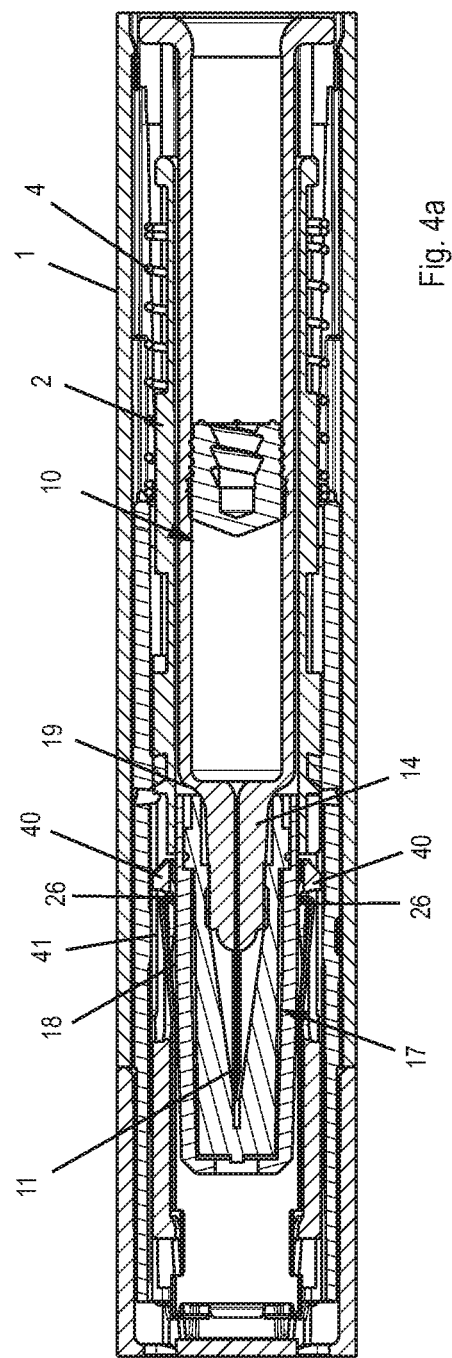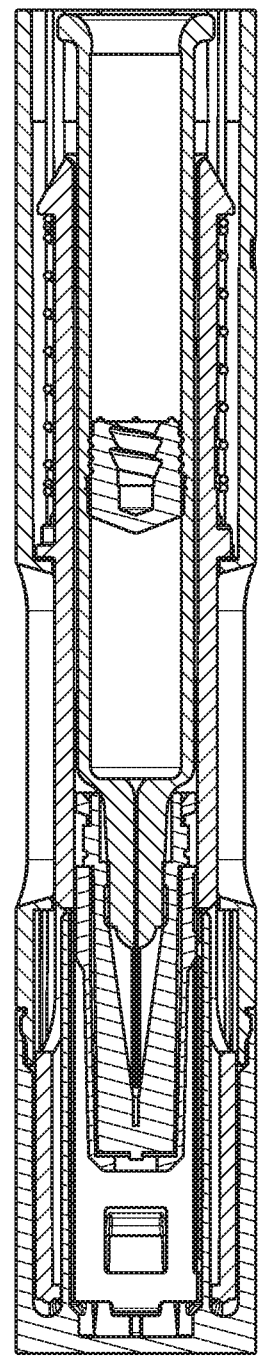
Fig. 4a
Fig. 4b

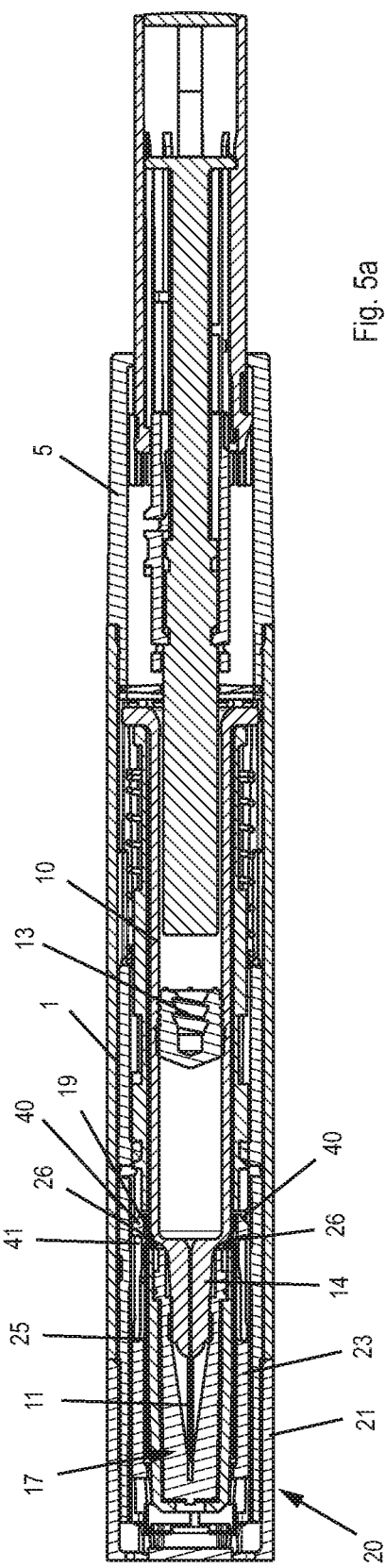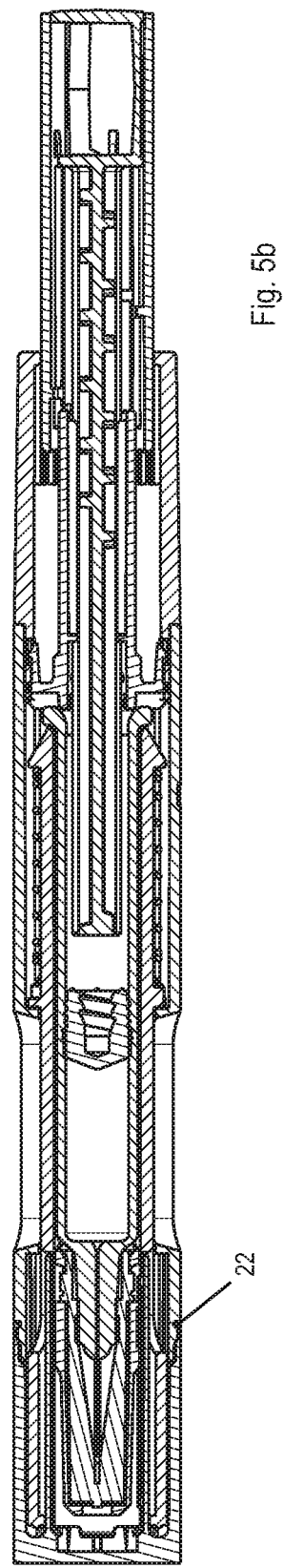

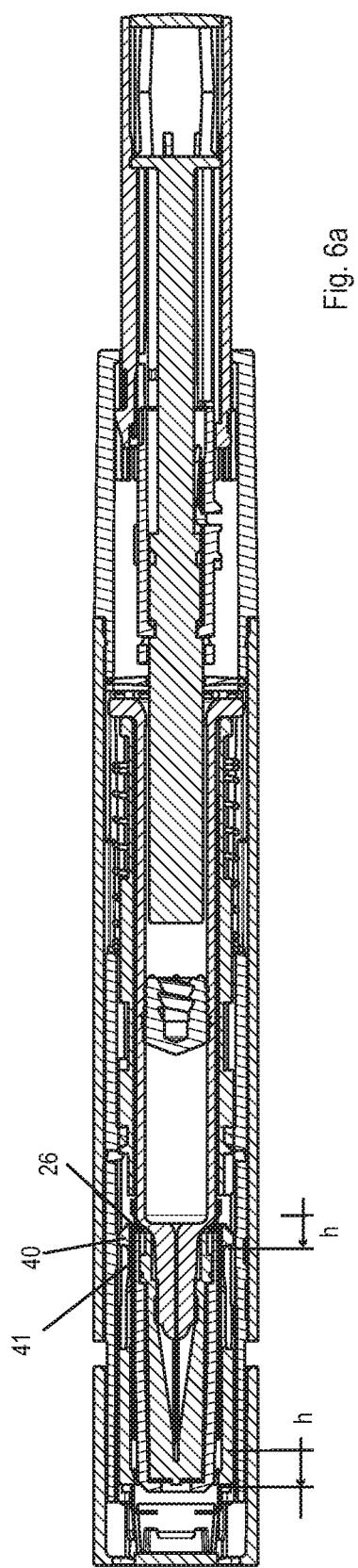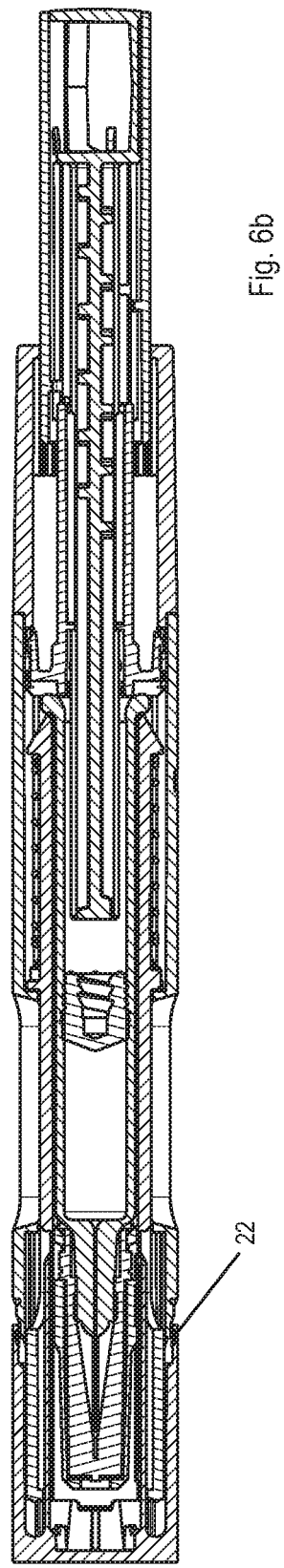

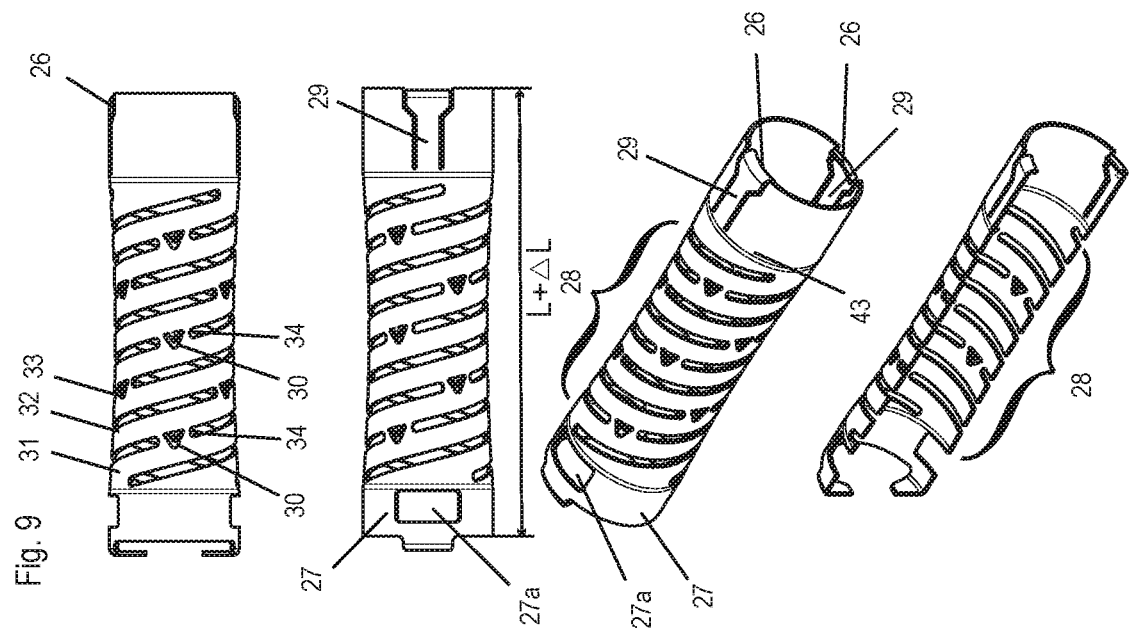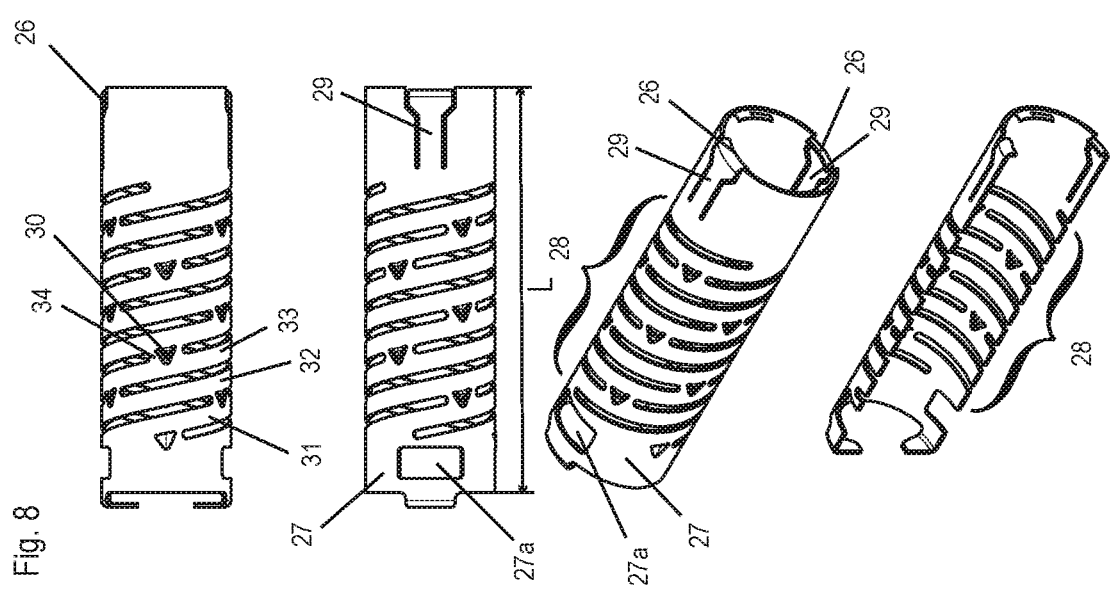

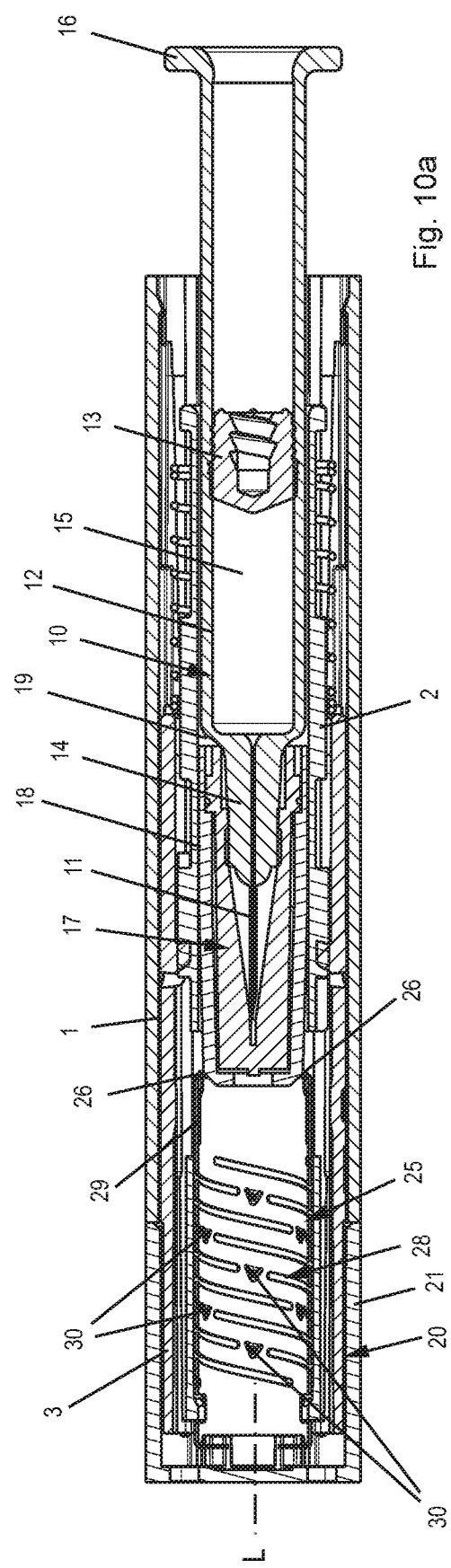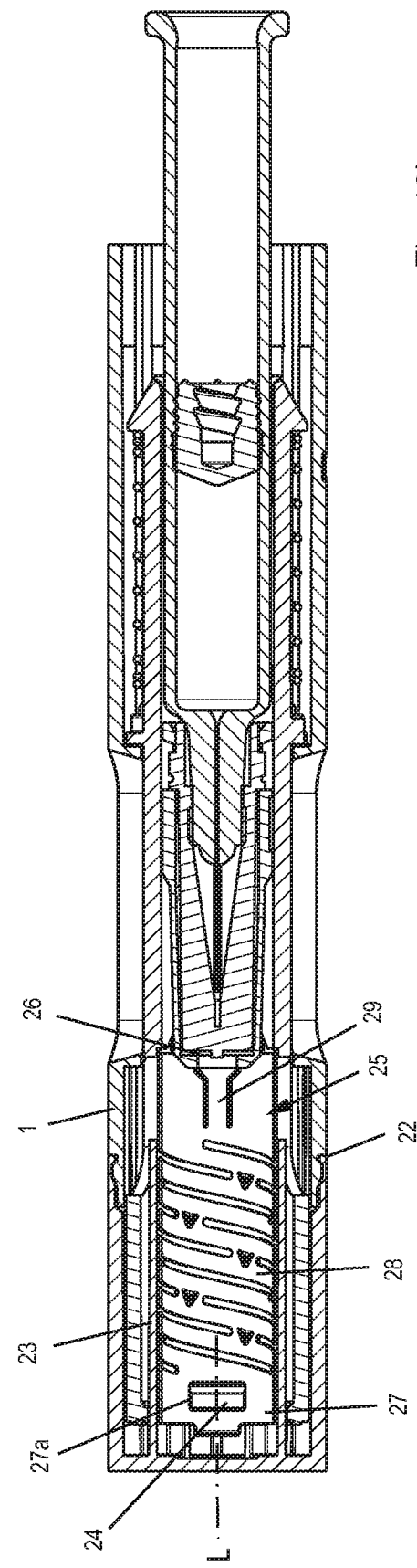

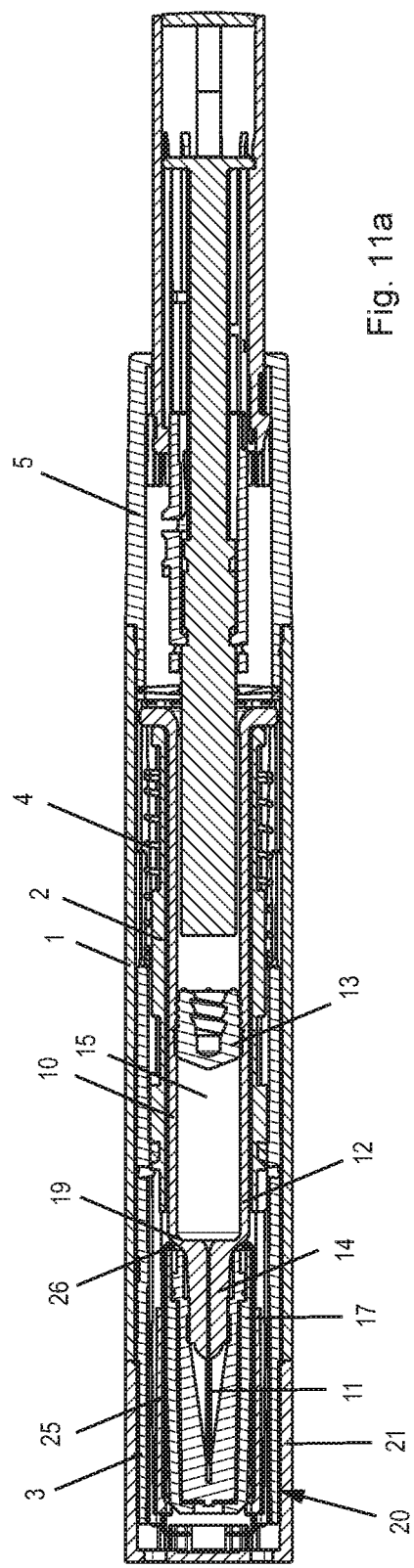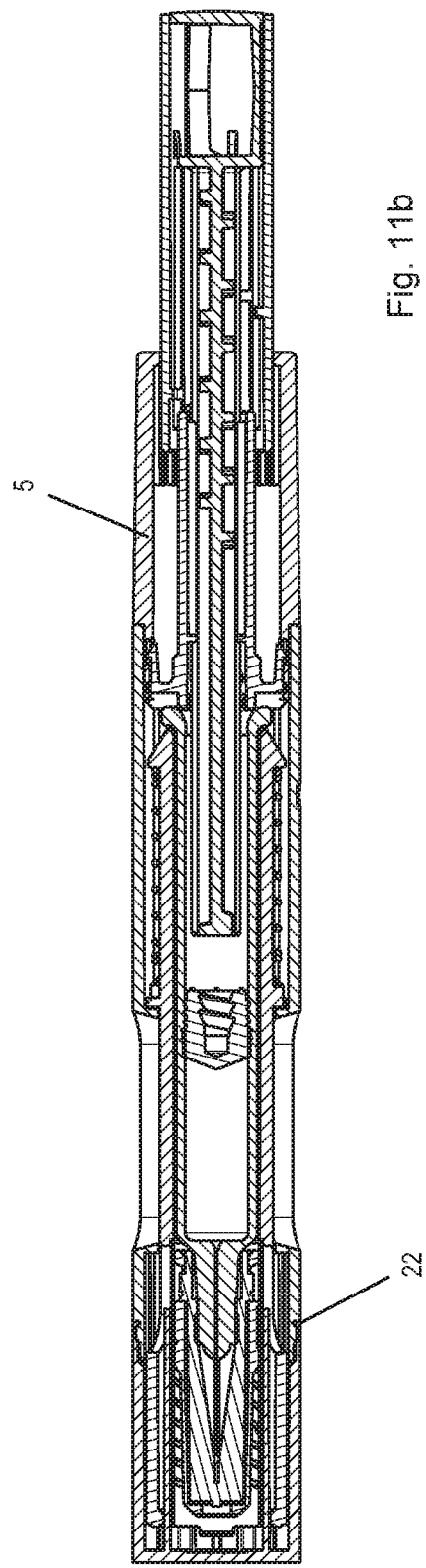

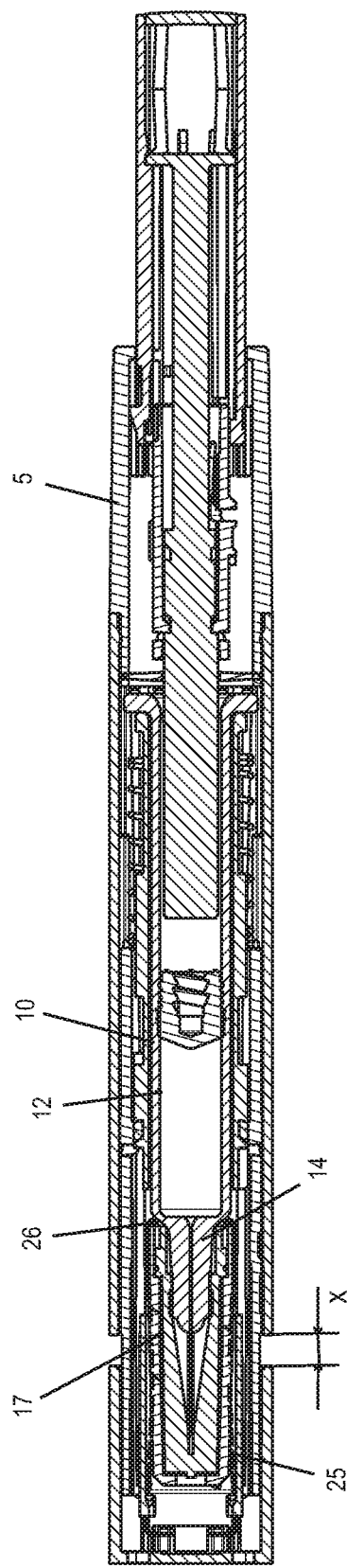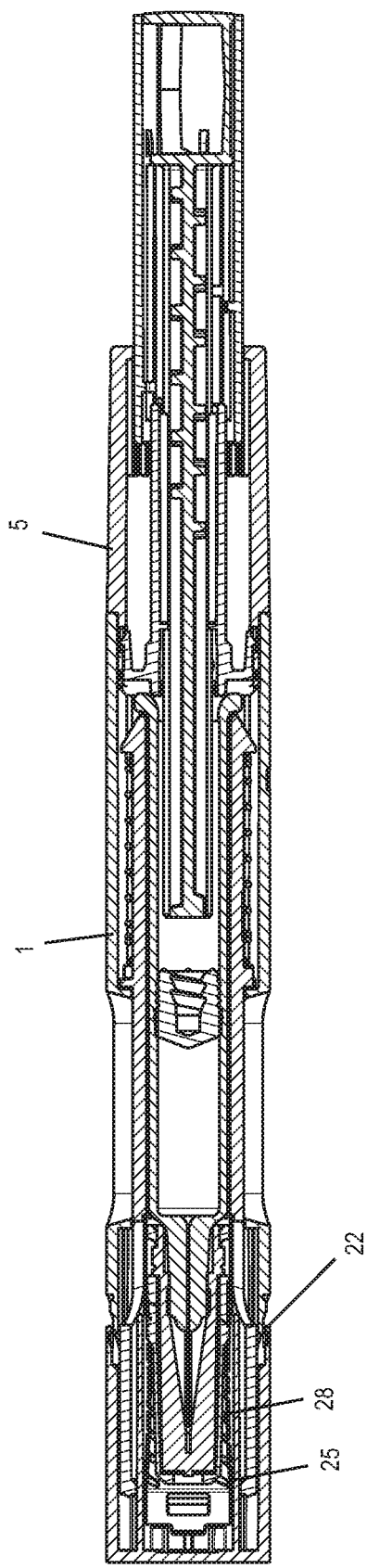

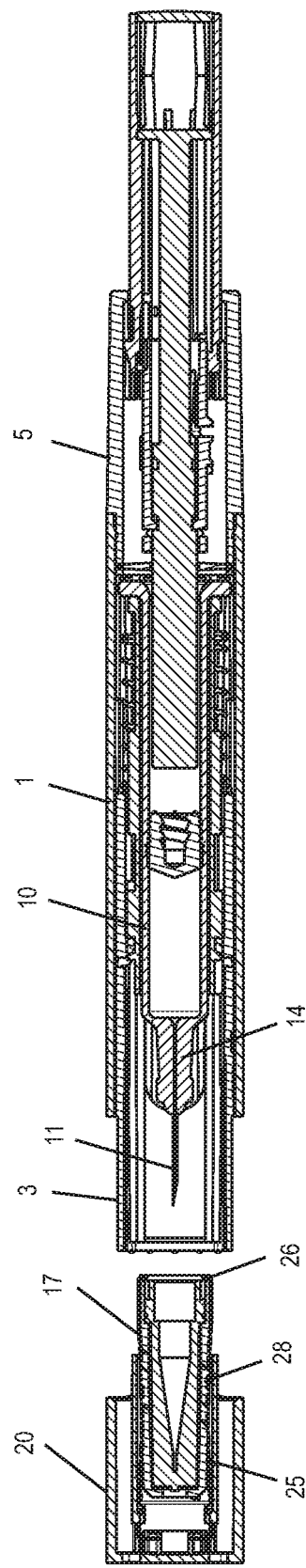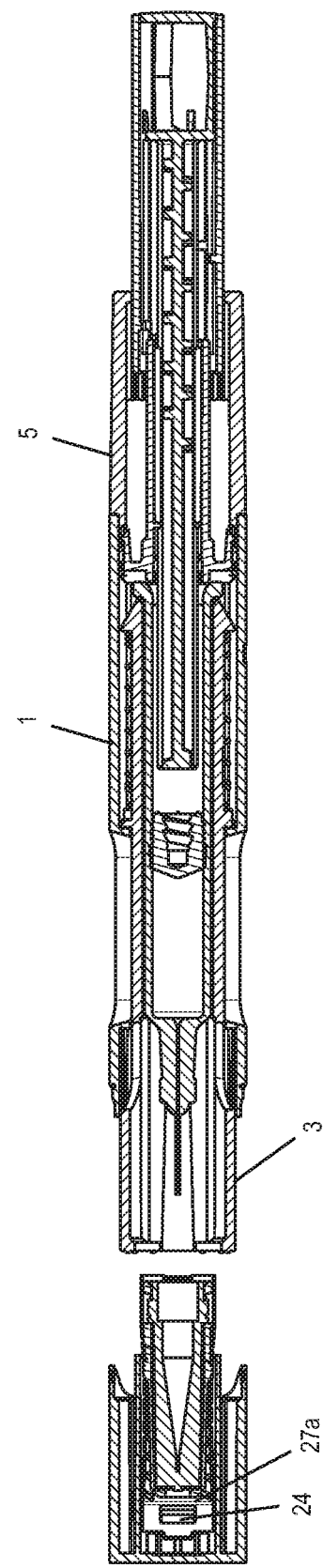

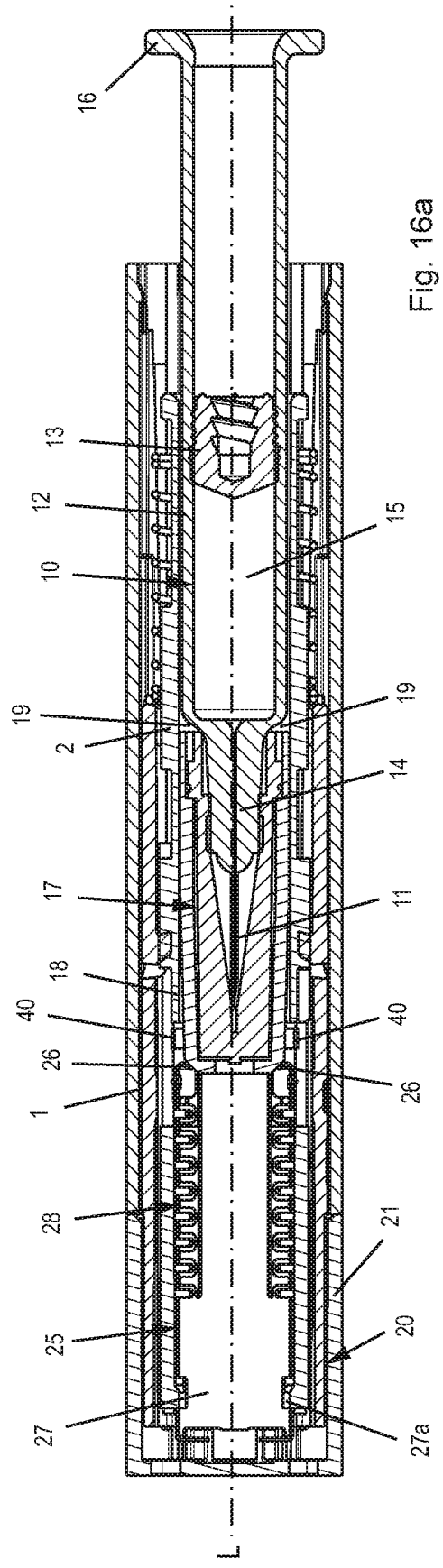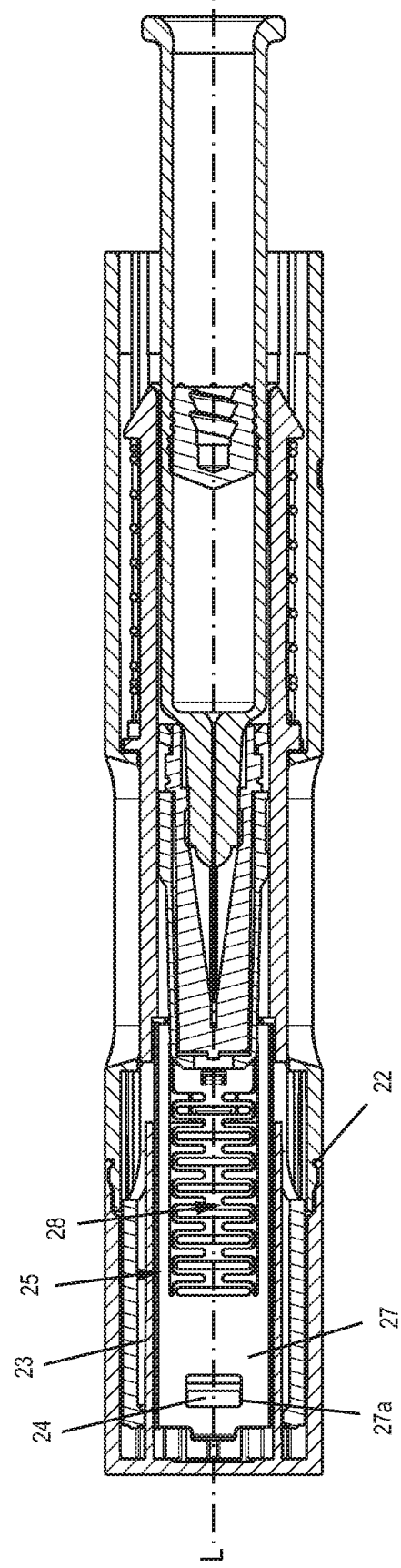

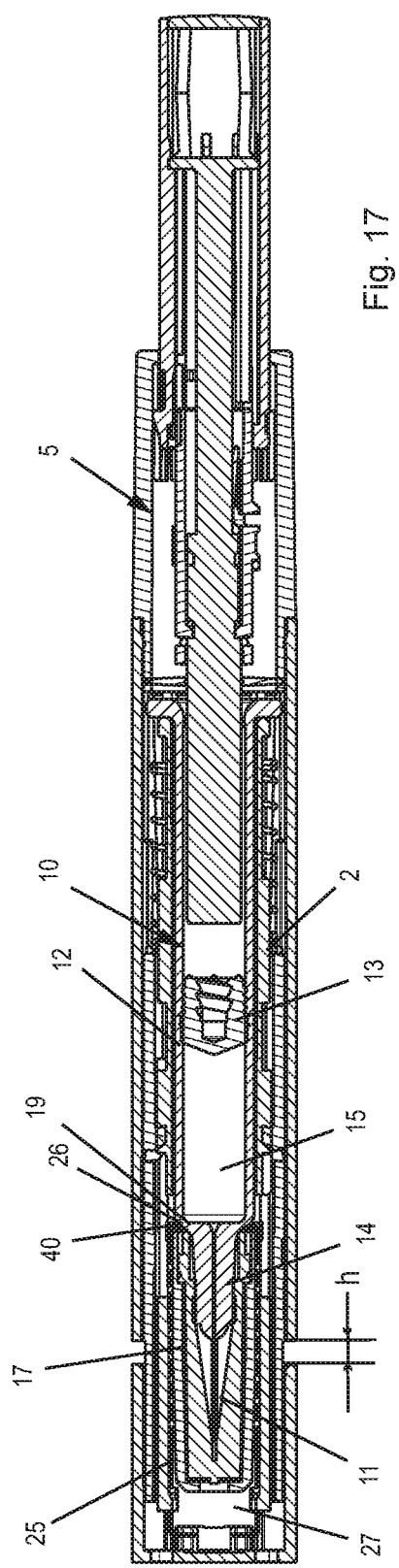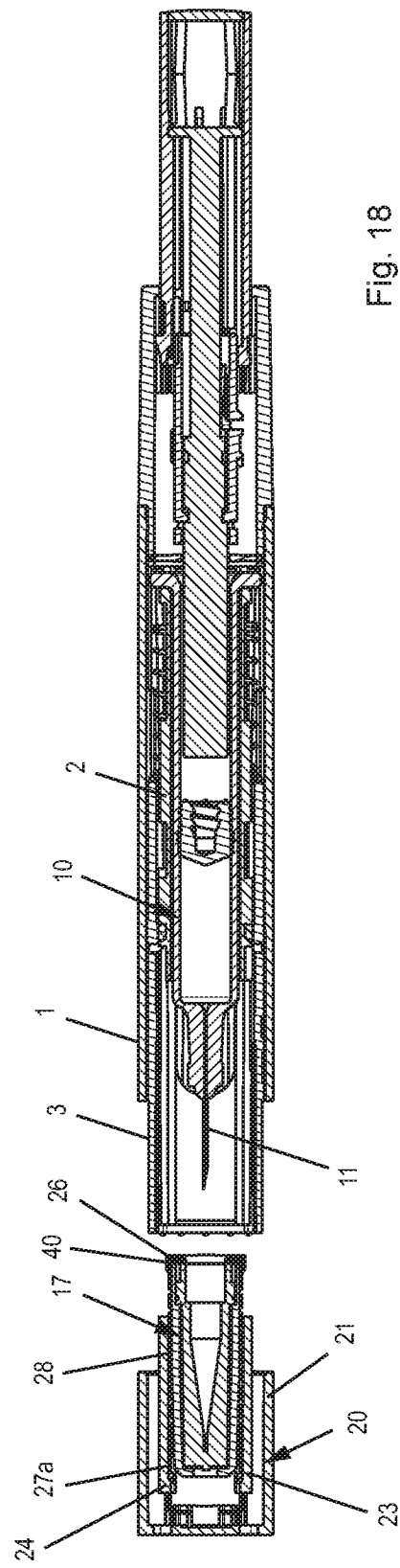

EXTERNAL CAP HAVING NEEDLE PROTECTION CAP REMOVER ELEMENT AND METHOD FOR ASSEMBLING AN INJECTION DEVICE

CROSS-REFERENCE TO RELATED APPLICATIONS

This application is a continuation of International Application No. PCT/CH2017/000062 filed Jun. 21, 2017, which claims priority to Swiss Application No. 00989/16 filed Jul. 28, 2016, the entire contents of all of which are incorporated by reference herein in their entirety.

FIELD OF THE INVENTION

The invention relates to an injection device for administering a liquid product, in particular a medicine. In particular, the invention relates to a mechanism for the injection device with which a needle protection cap placed on a product container can be released or removed from the product container. Moreover, the invention relates to a method for assembling an injection device and/or for preparing an injection device for the administration of a product.

BACKGROUND

The term "medicine" comprises any flowable medical formulation that is suitable for controlled administration through a means such as a cannula or hollow needle, e.g. comprising a liquid, a solution, a gel, or a fine suspension that contains one or more medical substance. A medicine can be a composition from a single container with a single active substance or a pre-mixed or co-formulated composition that has numerous active substances. Medicines comprise drugs such as peptides (e.g. medicines containing insulin, GLP-1, or preparations derived therefrom or analogous thereto), proteins and hormones, biological or active substances based on hormones or genes, nutrient formulas, enzymes and other substances, both in solid (suspended) or liquid forms, as well as polysaccharides, vaccines, DNS or RNS or oligonucleotides, antibodies or components of antibodies, and suitable base, auxiliary and carrier substances.

SUMMARY OF THE INVENTION

Injection devices are known from the prior art in which a pre-filled syringe is located. The pre-filled syringe has an injection needle connected permanently to the pre-filled syringe, and via which a medicine contained in the pre-filled syringe can be dispensed. In order to keep the injection needle or pre-filled syringe sterile, it is encompassed by a needle protection cap attached to the pre-filled syringe, and sealed off from the environment in a sterile manner. Such needle protection caps can be, e.g., a so-called soft needle shield or a rigid needle shield. A soft needle shield is made of an elastomer component that encompasses the needle. A rigid needle shield has numerous components, in particular an elastomer cap-shaped component and a component made of a solid, i.e. a non-elastomer plastic sheath-like component, which receives the elastomer component and is thus substantially connected thereto such that it cannot be released.

When handling the pre-filled syringe, there is the risk that the sterility of the needle is endangered by forces acting on the needle protection cap. This may occur during the assembly process of the injection device, in particular when the pre-filled syringe is placed in the syringe retainer of the injection device. The insertion of the pre-filled syringe into the injection device is a step requiring particular attention regarding the sterility of the needle. It is known from WO2010/136076 A1 that when removing a cap-shaped element, also referred to as a cap, placed on the distal end of the injection device and sealing the distal end of injection device, the needle protection cap placed on the syringe is also removed, i.e. when removing it, the cap is removed from the syringe. The needle protection cap remains in the cap. For this, the cap has engaging elements, which engage with the needle protection cap when the cap is removed. When the removal movement is continued, the engaging elements take the needle protection cap with them, by means of which it is removed from the product container. In order to ensure that the needle protection cap is removed when the cap is removed, it is known from the prior art for claw shaped elements made of metal, that are attached to the cap, to grip the circumference of the needle protection cap. This gripping already takes place during the assembly, because the needle protection cap is inserted into the region of the claw-like elements during the assembly of the injection device. The claw-like elements exert a certain amount of force, however, on the needle protection cap during the assembly, such that it cannot be ensured that the needle protection cap does not move in relation to the product container, thus endangering the sterility of the injection needle.

The object of the invention is to provide an injection device and a method for assembling and/or preparing an injection device for the administration of a product, which enables a simple placement of the product container in the injection device and/or a safe removal of the needle protection cap from the product container, without unintentionally endangering the sterility of the injection needle.

The object is achieved with the injection device according to claim 1 and the method according to claim 11. Advantageous further developments can be derived from the dependent claims, the description and the drawings.

The invention is based on a device for administering a product, specifically an injection device. The injection device can be a so-called auto-injector, which has a mechanism that automatically dispenses the product, e.g. by means of an energy storage element, in particular a spring, and optionally automatically inserts and/or removes the needle. With an auto-injector, the force needed for dispensing the product is provided by an energy storage element, e.g. the spring. The injection device can also be a manual injection device, i.e. the force needed for dispensing the product is provided by an external force, e.g. exerted by the user. The injection device can have a needle protection sleeve—regardless of whether it is an auto-injector or a manual injection device—which extends distally beyond the distal end of the injection needle after an injection, or is pushed into this position in relation to the housing, in order to prevent an unintentional access to the injection needle, and thus reduce the risk of injury. With an auto-injector, the needle protection sleeve can also be a triggering element for triggering the dispensing of the product, wherein the needle protection sleeve is displaced toward the housing.

The injection device has a product container with an injection needle, e.g. like a pre-filled syringe known from the prior art, or a syringe in general. The product container can have, e.g., a hollow cylindrical product container section with a piston. The piston can form a sealed gap with the inner circumference of the product container section. The piston can be displaced distally, e.g. by means of a piston rod of the injection device, in order to dispense a product from the product container via the injection needle. The injection needle can be formed on the product container, such that it cannot be removed therefrom. By way of example, the product container can have a retaining section, in particular a needle retaining section, which is located at the distal end of the product container section and is permanently connected to the injection needle, which encompasses a proximal part of the needle, for example. The injection needle can thus extend distally from the retaining section. The retaining section can have a smaller outer diameter than the product container section, for example. The product container section may be tapered at its distal end to the retaining section.

The term "distal" used herein relates to the direction in which the tip of the injection needle points. The term "proximal" used herein relates to the direction that is opposite to the distal direction. The distal end of the device is where the needle is located.

A needle protection cap is attached to the product container, e.g. at the retaining section, e.g. a soft needle shield or rigid needle shield known from the prior art, in particular such that it can be removed. The needle protection cap can be attached to the retaining section in a frictional or form-fitting manner, or in a combined frictional and form-fitting manner. The needle protection cap encompasses the injection needle and seals it off from the environment in a sterile manner. A soft needle shield comprises or is made of an elastomer, e.g. a component that has a synthetic or natural rubber basis, which encompasses the needle. The soft needle shield has a soft surface on its outer circumference, e.g. made of a synthetic or natural rubber. A rigid needle shield usually comprises numerous components, in particular an elastomer, cap-shaped inner component and a solid, i.e. non-elastomer plastic sleeve-shaped or cap-shaped outer component, which receives the elastomer component, and is thus substantially permanently connected thereto. The outer sleeve-like or cap-like component encompasses the inner cap-shaped component, and is permanently connected to the inner cap, for example, such that the outer and inner caps form a unit. The inner component can be made of a harder plastic than the inner component. The outer component can be made of plastic, e.g. of polyethylene, polystyrene, polypropylene, or another suitable plastic. The inner component can be made of synthetic or natural rubber, or another suitable material.

A cap, which can also be referred to or designed as an end cap or removable cap, can be attached to the distal end of the injection device or a housing, e.g. a receiving housing of the injection device, and close off the distal end of the housing or the receiving housing. The cap can be connected, e.g. in a frictional or form-fitting manner, to the housing or receiving housing, i.e. it can be snapped onto it. The cap can be removed from the injection device or the housing with an axial movement or a combined axial-rotational movement of the housing or receiving housing, for example. The word "cap" used alone, refers to the end cap or removable cap and not the needle protection cap.

The cap (e.g., end cap), which is coupled to one or more engaging elements, can be connected to the needle protection cap via at least one engaging element, such that the removal of the cap from the injection device results in the removal of the needle protection cap from the product container. In particular, at least part of the movement, or all the of the movement of the cap in the distal direction can be transferred to the engaging element, i.e., the engaging element is moved by cap, such that the engaging element pulls the needle protection cap off of the product container, in particular the retaining section.

The at least one engaging element is formed, e.g., by a sleeve-like removal element, which is attached to the cap. The cap can encompass the sleeve-like removal element, in particular it can surround the circumference thereof. The removal element is preferably separate from the cap, but is connected to the cap, e.g. such that it can be or cannot be displaced along the longitudinal axis thereof.

The engaging element can be engaged in the needle protection cap when the injection device is delivered. In the engaging position, the engaging element is located in relation to the needle protection cap such that a distal movement of the removal element moves the needle protection cap, thus removing the needle protection cap from the product container. In particular, a section of the needle protection cap can be axially aligned with the engaging element when in the engaging position, relative to the longitudinal axis of the injection device. This means that a part of the needle protection cap is located distally in front of the engaging element, when viewed from the perspective of the engaging element, such that when the engaging element is moved distally, the needle protection cap is moved with it. By way of example, the engaging element can engage with or in the needle protection cap when it is in the engaging position.

The cap and the engaging element can be coupled, in particular such that the cap is or can be moved in relation to the engaging element when it is removed from the injection device, in particular the housing or receiving housing. This results in the advantage that, through this movement, other components or sections of the injection device can be positioned such that the connection of the removal element is secured, or even reinforced with the needle protection cap, by means of which it is ensured that the needle protection cap is safely removed from the product container when the cap is removed. There is also the advantage that components or sections of the removal element, e.g. the at least one engaging element, can be formed such that the forces exerted by them on the needle protection cap when inserting the product container are low. This prevents movement of the needle protection cap in relation to the product container when the product container is inserted. This reduces the risk of contamination to the needle.

By way of example, the cap and the engaging element can be coupled such that the cap can first be moved or is moved in relation to the engaging element during the removal of the cap from the injection device, and the engaging element subsequently is moved with the cap, e.g. by the cap, or the movement of the cap, by means of which the needle protection cap is removed from or pulled off of the product container. In other words, the distal movement of the cap in relation to the housing along the longitudinal axis thereof during the removal from the injection device comprises a first sub-movement, during which the cap can move or is moved in relation to the engaging element, and a second sub-movement, during which the engaging element moves with the cap or is moved by the cap. The engaging element can be secured during the first sub-movement such that it cannot be brought out of its engaging position, while the needle protection cap during the second sub-movement is removed from the product container, and the injection needle is exposed.

By way of example, the injection device can have a blocking section, which can be or is moved from a releasing position to a blocking position, in particular during the first sub-movement, or when the cap is moved in relation to the engaging element during the removal from the injection device. The blocking section is formed such that it blocks movement of the engaging element from the engaging position and/or an outward movement transverse to the longitudinal axis, i.e. away from the longitudinal axis, when the blocking section is in a blocking position. The blocking section is configured such that it does not block outward transverse movement of the engaging element when the blocking section is in its releasing position. By way of example, the blocking section can be coupled to the cap such that the removal of the cap from the housing, in particular the receiving housing, moves the blocking section from the releasing position to the blocking position, in particular during the first sub-movement or when the cap is moved in relation to the engaging element, in particular during the distal movement of the cap along the longitudinal axis.

By way of example, the blocking section can have a surface facing inward, or toward the longitudinal axis, which is located along the longitudinal axis at the height or position of the engaging element when in the blocking position, by means of which the engaging element is prevented from moving outward, transverse to the longitudinal axis. In particular, the engaging element is located between the blocking section and the longitudinal axis of the injection device when the blocking section is in the blocking position.

By way of example, the cap can have a recess, which is at the height of in the position of the engaging element along the longitudinal axis when the blocking section is in the releasing position, wherein the blocking section is moved to the blocking position by removing the cap, in particular during the first sub-movement. In particular, the engaging element can be located between the recess and the longitudinal axis, when the blocking section is in the releasing position. In particular, the recess can be designed such that it cannot prevent or block an outward movement of the engaging element transverse to the longitudinal axis.

In particular, the cap can form or contain the blocking section, wherein it is preferred that the blocking section is proximal to the recess.

When the blocking section is formed by the removal element, for example, the blocking section and the engaging element can be connected by a malleable section, which becomes deformed in an elastic or plastic manner during the movement of the blocking section from the releasing position to the blocking position. In particular the malleable section can be flexible. The malleable section can have a coupling section, for example, which is coupled to or engaged in the cap such that it cannot move, or can only move to a limited extent, axially along the longitudinal axis. The malleable section can be helical or meandering, such that it can be deformed along the longitudinal axis. The blocking section can be rigidly connected to the coupling section, for example, such that the coupling section and the blocking section cannot be moved, or cannot be noticeably moved along the longitudinal axis in relation to one another.

In general, the e.g. sleeve-like removal element can have a coupling section, which can be engaged with the cap such that it cannot move axially, or can only be moved to a limited extent axially. By way of example, the coupling section can have a recess in which a projection on the cap engages.

By way of example, the blocking section can be proximal to the engaging element and/or the proximal end of the needle protection cap when in its releasing position.

In preferred embodiments, the malleable section or the engaging element can have an axial stop, which the blocking section strikes when it is moved from its releasing position to the blocking position, or the cap is removed from the injection device. The stop element can be a lug, for example, which protrudes outward, i.e. away from the longitudinal axis, and is radially aligned with the blocking section along the longitudinal axis.

In an alternative embodiment, the removal element, in particular the coupling section or the recess of the coupling section in which the cap engages, can have an axial stop, which the cap strikes, like the projection at the end of the first sub-movement, by means of which the cap can remove the removal element after completion of the first sub-movement.

In preferred embodiments, the cap and the removal element can be engaged, such that a coupling section of the removal element, which is connected to the engaging element via a malleable section that encompasses the circumference of the needle protection cap is moved by the cap when the cap is removed from the receiving housing. As a result, the coupling section can move in relation to the engaging element, and the malleable section can be deformed such that the malleable section constricts the circumference of the needle protection cap, or presses against the circumference of the needle protection cap. As a result, the friction, for example, between the needle protection cap and the malleable section is increased and/or a form fit is produced between the needle protection cap and the malleable section. As a result, the force required for removing the needle protection cap from the cap that is applied to the needle protection cap is not, or not only, transferred from the engaging element to the needle protection cap, but instead, is also transferred via the malleable section.

By way of example, the malleable section can have one or more engaging lobes, which press into the circumference of the needle protection cap as a result of the constriction of the malleable section. Alternatively or additionally, the malleable section can have at least one, e.g. a single, two, three, four, or more spirals, which wind with one or more windings about the longitudinal axis of the injection device, and connect the coupling section to the engaging element. As a result of the helical design of the malleable section, the constriction thereof causes a reduction in the inner diameter when the spacing between the coupling section and the engaging element is increased along the longitudinal axis. Adjacent windings of the spirals can be connected to one another, e.g. via one or more connecting webs. The webs increase the fundamental stability of the removal element, e.g. for it capacity for containing bulk goods and with respect to assembly thereof.

Without these connecting webs, the malleable section would be extremely flexible (like a spring), which would make the assembly of the removal element extremely difficult.

The invention also relates to a method for assembling an injection device and/or for preparing an injection device for administering a product. The injection device can be the injection device described herein, for example.

The method comprises the step of providing a receiving housing, which can be part, e.g., of a housing for the injection device, for receiving a product container. The receiving housing can be sleeve-shaped and/or elongated. The cap can be placed on the distal end of the receiving housing, e.g. snapped onto it, wherein the removal element, which has the engaging element that can move transverse to the longitudinal axis of the receiving housing, is located in the cap.

The method also comprises the step of providing the product container, which has a product container section and an injection needle connected to the product container section, wherein the product container section has a displaceable piston, wherein the product is located between the injection needle and the piston. The needle protection cap is located on the product container and encompasses the injection needle, preferably sealing it against the environment in a sterile manner.

The method also comprises the distal displacement of the product container, including the needle protection cap attached thereto in the longitudinal axis and along the longitudinal axis in relation to the receiving housing. Optionally, the product container, along with the needle protection cap attached thereto, can be inserted into the receiving housing via the proximal end, at which the receiving housing has an opening, in particular with the needle protection cap at the front.

The engaging element of the removal element is deflected by an outer surface or outer circumference of the needle protection cap during the displacement of the product container in the distal direction along the longitudinal axis, along with the needle protection cap. Because the sleeve-like removal element has numerous, e.g. two, engaging elements, which are opposite one another over the circumference, the engaging elements can be spread apart, in particular away from the outer surface or outer circumference of the needle protection cap. In general, the engaging element is basically deflected radially outward, i.e. away from the longitudinal axis, by the needle protection cap. The outer surface or outer circumference of the needle protection cap slides along the engaging element during the displacement of the product container, along with the needle protection cap attached thereto. The engaging element is moved into an engaging position at the end of the displacement of the product container with a movement transverse to the longitudinal axis. The engaging element can be placed in a spring-loaded manner on, for example, the removal element, by means of which it is pushed by spring force, transverse to the longitudinal axis, into the engaging position. A distal section of the needle protection cap is axially aligned with the engaging element relative to the longitudinal axis L when in the engaging position. In particular, the section is distal to the engaging element, by means of which the engaging element is pressed against or strikes the needle protection cap or the proximal end of the needle protection cap when the removal element, together with the cap, is moved distally in relation to the needle protection cap.

The product container section of the injection device described herein can be tapered at its distal end, and transition, e.g., into a needle retaining section. A gap can be formed, for example, between the tapered end and the proximal end of the needle protection cap, in which the engaging element is moved or pushed by spring force into the engaging position at the end of the displacement of the product container with a movement transverse to the longitudinal axis and toward the longitudinal axis.

In embodiments with a blocking section, the blocking section is in the releasing position, in particular such that it is offset proximally to the engaging element when the product container, along with the needle protection cap attached thereto, is inserted in the distal direction into the receiving housing along the longitudinal axis. As a result, the at least one engaging element on the removal element can advantageously be designed such that there is only a slight resistance to a transverse outward deflection of the engaging element, i.e. basically radially away from the longitudinal axis, such that the deflection of the engagement elements by the needle protection cap does not result in a displacement of the needle protection cap on the product container, such that the sterility of the needle is not endangered during the displacement of the product container in the receiving housing during the assembly of the injection device. In particular, a recess may be located at the position of the engaging element in relation to the longitudinal axis.

The blocking section—as specified above—can be moved from the releasing position to the blocking position. It is in the releasing position when the cap is placed entirely on the receiving housing, e.g. snapped onto it, and the product container, along with the needle protection cap, is displaced distally. The blocking section does not block the transverse outward movement of the engaging element when the blocking section is in its releasing position, and blocks a transverse outward movement of the engaging element when the blocking section is in its blocking position.

The blocking section is then also in its releasing position when the injection device is fully assembled. The blocking section is first moved distally from the releasing position to the blocking position for preparing an injection, i.e. by removing the cap from the injection device or its housing, and not already during the assembly of the injection device.

By way of example, the blocking section can be formed by the cap or the removal element. By way of example, the cap can have a recess, which is in a position at the height of the engaging element along the longitudinal axis, when the blocking section is in the releasing position, wherein the blocking section is moved into the blocking position by removing the cap. Alternatively, the blocking section formed by the removal element and the engaging element can be connected via a malleable section of the removal element, which becomes deformed during the movement of the blocking section from the releasing position to the blocking position, in particular such that it is elongated along the longitudinal axis.

In embodiments in which the cap and the removal element are engaged, such that a section of the removal element that is connected to the engaging element via a malleable section that encompasses the circumference of the needle protection cap, which is also removed from the cap when the cap is removed from the receiving housing, the section, in particular the coupling section, is moved in relation to the engaging element, and the malleable section becomes deformed. As a result, the malleable section is constricted against the circumference of the needle protection cap. By this means, the friction between the needle protection cap and the malleable section can be increased, and/or a form fit can be obtained between the needle protection cap and the malleable section. By way of example, the malleable section can have one or more engaging lobes, which press into the circumference of the needle protection cap through the constriction of the malleable section.

In addition, reference is made to the features disclosed in conjunction with the device described herein, which also advantageously further develop the device for the method.

BRIEF DESCRIPTION OF THE DRAWINGS

The invention shall be described below based on numerous exemplary embodiments and examples. Particularly preferred embodiments shall be explained in greater detail below based on the figures. The features disclosed thereby advantageously form the invention, individually and in any combination of features. Therein:

FIG. 1 shows a sectional view of a cap with a removal element located thereon, to form a first embodiment of the invention, FIG. 2 shows the removal element in FIG. 1, FIGS. 3a and 3b show sectional views of a receiving housing for an injection device with the cap shown in FIG. 1 and a product container that has been partially inserted, wherein FIG. 3b shows a perspective rotated 90° about the longitudinal axis in relation to FIG. 3a, FIGS. 4a and 4b show the assemblies in FIGS. 3a and 3b during the distal displacement of the product container in relation to the receiving housing, prior to reaching the distal end position, wherein FIG. 4b shows a perspective rotated 90° about the longitudinal axis in relation to the FIG. 4a, FIGS. 5a and 5b show sectional views of an injection device with the assemblies shown in FIGS. 4a and 4b, wherein the product container is in a distal end position in relation to the receiving housing, wherein FIG. 5b shows a perspective rotated 90° about the longitudinal axis in relation to FIG. 5a, FIGS. 6a and 6b show the injection device shown in FIGS. 5a and 5b, wherein the cap is released from the receiving housing, and moved distally in a first sub-movement, wherein FIG. 6b shows a perspective rotated 90° about the longitudinal axis in relation to FIG. 6a, FIGS. 7a and 7b show the injection device shown in FIGS. 6a and 6b, wherein the cap, along with the needle protection sleeve, is removed from the receiving housing, or the needle protection sleeve is removed from the product container, wherein FIG. 9 shows the illustrations in FIG. 8, wherein the malleable section of the removal element extends along the longitudinal axis, thus having a constricted diameter, FIGS. 10a and 10b show sectional views of a receiving housing for an injection device with a cap attached to a distal end of the receiving housing, in which the removal element from FIG. 8 is located, wherein a product container has been partially inserted into the receiving housing, wherein FIG. 10b shows a perspective rotated 90° about the longitudinal axis in relation to FIG. 10a, FIGS. 11a and 11b show sectional views of an injection device with the assemblies from FIGS. 10a and 10b, wherein the product container has been pushed into a distal end position in relation to the receiving housing, and a drive housing is attached to the proximal end of the receiving housing, wherein FIG. 11b shows a perspective rotated 90° about the longitudinal axis in relation to FIG. 11a, FIGS. 12a and 12b show the injection device from FIGS. 11a and 11b, wherein the cap is released from the receiving housing, and displaced by a sub-movement in relation to the receiving housing, resulting the constriction of the malleable section as shown in FIG. 9, wherein FIG. 12b shows a perspective rotated 90° about the longitudinal axis in relation to FIG. 12a, FIGS. 13a and 13b show the injection device from FIGS. 12a and 12b, wherein the cap, along with the needle protection sleeve is removed from the receiving housing, wherein FIG. 13b shows a perspective rotated 90° about the longitudinal axis in relation to FIG. 13a, FIG. 14 shows various perspectives of a removal element for a third embodiment of the invention, FIGS. 16a and 16b show sectional views of an assembly that has a receiving housing with a cap attached to the distal end, which receives the removal sleeve shown in FIG. 14, wherein a product container has been partially inserted into the receiving housing, wherein FIG. 16b shows a perspective rotated 90° about the longitudinal axis in relation to FIG. 16a, FIG. 17 shows a sectional view of an injection device that has the assembly shown in FIG. 16a, wherein the cap is released from the receiving housing, and has been distally displaced by a first sub-movement along the longitudinal axis, FIG. 18 shows the injection device from FIG. 17, wherein the cap has been removed, along with the needle protection sleeve, from the receiving housing.

DETAILED DESCRIPTION

Figure 7A:
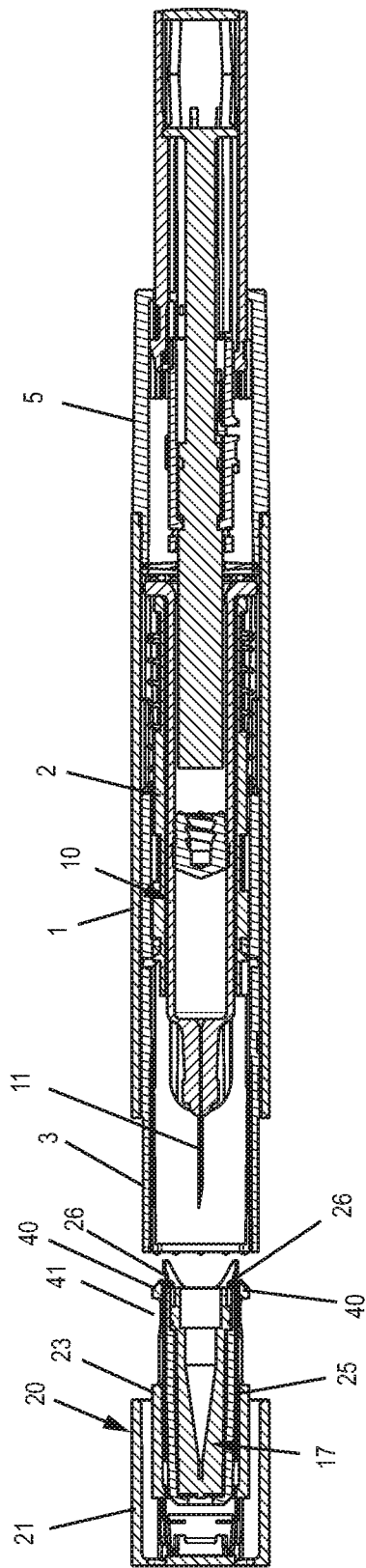
FIG. 7b shows a perspective rotated 90° about the longitudinal axis in relation to FIG. 7a, FIG. 8 shows various perspectives of a removal element for a second embodiment of the invention.
Figure 7B:
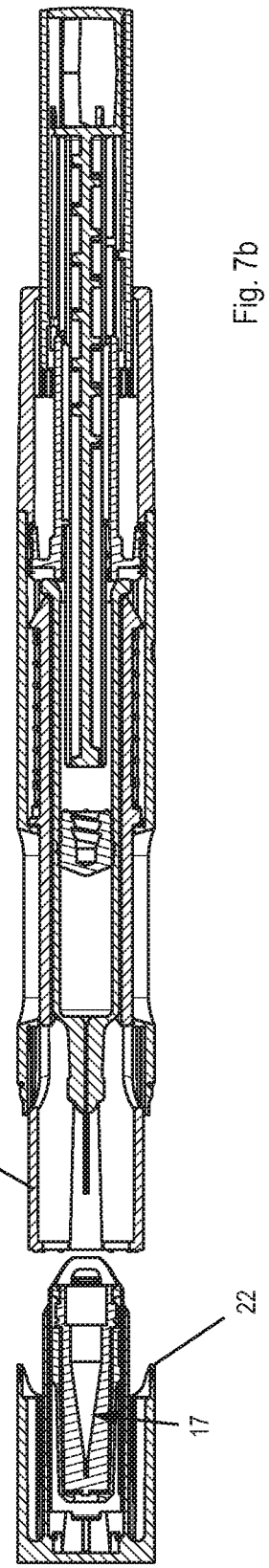

The first embodiment, which is shown in FIGS. 1 to 7b, the second embodiment, which is shown in FIGS. 8 to 13b, and the third embodiment, which is shown in FIGS. 14 to 18, all involve the process of placing a product container 10 in the injection device. The injection device has a sleeve-like, in particular cylindrical, receiving housing 1 with a proximal end and a distal end. A cap 20 is located on the distal end of the receiving housing 1, and attached to the receiving housing 1. The cap 20 has a sleeve section 21, which extends like the receiving housing 1 over a longitudinal axis L of the injection device or the receiving housing 1. The distal end of the sleeve section 21 is substantially closed, such that there is no access to the interior of the cap 20 from the outside, or the interior can only be accessed with difficulty. The cap 20 is connected in a form fitting manner to the receiving housing 1, in particular in that it is snapped onto it. The cap 20 has an engaging element 22 at its proximal end, which engages in a corresponding counter-engaging element of the receiving housing 1, in particular in that it is snapped onto it. The form fitting engagement can be released by a movement of the cap 20 about and/or along the longitudinal axis L, by means of which the cap 20 can be removed from the receiving housing 1 with a movement along the longitudinal axis L.

A preferably sleeve-like removal element 25, also referred to or designed as a removal sleeve 25, is received such that it can or cannot be displaced along the longitudinal axis L in relation to the cap 20—depending on the embodiment.

A drive unit, which has a drive housing 5, can or is attached to the proximal end of the receiving housing 1. The drive housing 5 can be joined to the receiving housing 1, e.g. in a force fitting and/or form fitting and/or material bonded manner. The drive housing 5 can encompass a piston rod, for example, which can be a component of the drive unit. By displacing the piston rod distally, a product is dispensed from a product container 10.

A product container 10 in the form of a syringe is located in the receiving housing 1. The product container 10 has a product container section 12, which forms a hollow cylinder in particular, and its inner wall forms a sealed gap with a piston 13 that can be displaced in the product container section 12. The proximal end of the product container section 12 can optionally have a flange 16, also referred to as a finger flange. The product container section 12 tapers at its distal end to form a needle retaining section 14, which has a significantly smaller outer diameter than the product container section 12. The needle retaining section 14 encompasses the proximal part of an injection needle 11 and is preferably permanently connected thereto. The injection needle 11 extends distally from the needle retaining section 14. By displacing the piston 13 distally, the preferably liquid product located between the injection needle 11 and the piston 13 in the product container section 12 can be dispensed through the injection needle 11.

A needle protection cap 17 is releasably attached, e.g. in form fitting and/or frictional manner, to the needle retaining section 14. The needle protection cap 17 can be a so-called rigid needle shield or a soft needle shield. The needle protection cap 17 encompasses the injection needle 11 such that the sterility thereof is ensured in relation to the environment of the needle protection cap 17.

The product container 10 can optionally be located in, e.g., a sleeve-like product container retainer 2, and tightly retained therein. By way of example, the tapered section of the product container section 12 can be braced distally on an inner shoulder of the product container retainer 2. Alternatively, the flange 16 can be distally braced on the product container 2. In another alternative, the product container retainer 2 can retain the product container 10 at its product container section 12 in a frictional manner. The product container retainer 2 can be located in the receiving housing 1 such that it can or cannot move axially.

A needle protection sleeve 3 can optionally be located in the receiving housing 1, which can be displaced proximally in relation to the receiving housing 1 in order to initiate a product dispensing, and can be displaced distally after dispensing the product, in order to cover the tip of the injection needle 11, in order to reduce risk of injury. Such needle protection sleeves 3 are known from the prior art, however, and can be regarded as an advantageous further development of the invention.

According to the first embodiment shown in FIGS. 1 to 7b, the sleeve-like removal element 25 is placed in the cap 20. The cap 20 and a coupling section 27 of the removal element 25 interact such that the cap 20 can be moved distally in relation to the coupling section 27 to a limited extent, in particular by a movement h (FIG. 3a) along the longitudinal axis L. The removal element 25 forms an axial stop in particular, which a part of the cap 20 strikes at the end of the movement h, thus causing the removal element 25 to be removed from the cap 20 when the cap 20 is moved distally along the longitudinal axis L and in relation to the receiving housing 1. The movement h can also be referred to as the first sub-movement of an overall movement necessary, e.g., for removing the cap 20 from the receiving housing 1.

The coupling section 27, or the removal element 25 in general, has a recess 27a, in which a projection 24 formed by the cap 20 engages. The distal end of the recess 27a forms the axial stop for the projection 24, wherein the projection 24 strikes the distal end of the recess 27a at the end of the first sub-movement h. When the cap 20 is fully placed on the receiving housing, i.e. when the cap 20 is snapped onto the receiving housing 1, the spacing between the distal end of the recess 27a and the projection 24 is basically as far as the first sub-movement h (FIG. 3a).

The cap has an inner sleeve 23, which is located in the sleeve section 21 and is basically concentric thereto, and surrounds or tightly encompasses the external circumference of the removal element 25. As a result, the removal element 25 can be guided by the cap 20 along the longitudinal axis L. By guiding the removal element 25 through the inner sleeve 23, a lateral tilting of the removal element 25 can be safely prevented.

The removal element 25 has an engaging element 26, which is attached to the coupling section 27 via an arm, in particular a spring arm. The arm 29 is designed such that it allows a movement of the engaging element transverse to the longitudinal axis L, in particular in a radial direction thereto. In particular, the engaging element 26 can be moved radially outward, i.e. away from the longitudinal axis L, and pushed back to its original position by spring force, i.e. toward the longitudinal axis L.

The removal element 25 has a hook-like or inward extending engaging element 26, which is in an engaging position in relation to the needle protection cap 17 when the injection device is fully assembled, wherein when it is in the engaging position, a section of the needle protection cap 17 is axially aligned with engaging element 26 (at its location) relative to the longitudinal axis L. In the examples in the figures, the engaging element 26 engages in a gap between the proximal end of the needle protection cap 17 and the tapered transition from the product container section 12 to the needle retaining section 14. Alternatively, when the engaging element 26 is in its engaging position, it could engage in a recess in the outer circumference of the needle protection cap, or engage in the outer circumference of the needle protection cap 17 through a deformation of the needle protection cap 17 when the injection device is fully assembled.

FIGS. 4a and 4b show the position of the engaging element 26 when the product container 10 is inserted in the distal direction, prior to reaching the distal end position.

The injection device is shown in its fully assembled state in FIGS. 5a and 5b, wherein the engaging element 26 is in the engaging position. The cap 20 has a blocking section 40, which is in a releasing position proximal to the engaging element 26. When the cap 20 is removed, the engaging element 26 is released from the corresponding engaging element in the receiving housing 1, and the cap is moved distally along the longitudinal axis L. The cap 20 makes a first sub-movement h along the longitudinal axis L in the distal direction, by means of which the blocking section 40 is likewise moved in relation to the engaging element 26 by the first sub-movement h in distal direction (FIGS. 6a, 6b). At the end of the first sub-movement h, the cap 20, in particular its projection 24 strikes the axial stop of the removal element 25, in particular the distal end of the recess 27a, and the blocking section 40 is then in its blocking position, specifically a position in which it blocks the transverse outward movement of the engaging element 26, or away from the longitudinal axis L (FIGS. 6a, 6b). When the cap 20 is moved further along the longitudinal axis L in the distal direction, the removal element 25 and thus also the engaging element 26 and the needle protection cap 17, are also moved therewith, e.g. during a second sub-movement, by means of which the needle protection cap 17 is removed from the product container 10, in particular the needle retaining section 14. The needle protection cap 17 is thus removed with the cap 20 from the injection device or the receiving housing 1, by means of which the injection needle 11 is exposed for a subsequent injection. By positioning the blocking section 40 in the blocking position, the engaging element 26 is prevented from disengaging from the needle protection cap 17 when the cap 20 is pulled off of the receiving housing 1. This ensures that the needle protection cap 17 is always removed with the cap 20.

As a result of the engagement of the projection 24 in the recess 27a, the removal element 25 is connected to the cap 20 such that it cannot rotate about the longitudinal axis L.

The third embodiment illustrated in FIGS. 14 to 18 has the sleeve-like removal element, which is connected at its coupling section 27 to the cap 20 such that it is axially fixed in position, i.e. it cannot be displaced along the longitudinal axis L. The cap 20 has a projection 24, which engages in the recess 27a in the coupling section 27. The removal element 25 is connected to the cap 20 such that it cannot rotate about the longitudinal axis L, in particular by means of the engagement of the projection 24 in the recess 27a.

The engaging element 26 is connected to the coupling section 27 via a malleable section 28. The malleable section 28 is designed such that it can be deformed along the longitudinal axis L, and in particular also transverse to the longitudinal axis L. In particular, it can be deformed such that its length L along the longitudinal axis L can be extended by ΔL.

The malleable section 28 can have one or more sections or webs that wind in a spiral or meander along the longitudinal axis L, which connect the coupling section 27 and the engaging element 26. Alternatively or additionally, the malleable section 28 can have numerous annular elements distributed along the longitudinal axis L, wherein adjacent annular elements are connected via a connecting web. The annular axis about which the rings extend is transverse to the longitudinal axis L, in particular substantially perpendicular thereto. In particular, the rings can be flattened along the longitudinal axis L such that each of the rings encompasses a slot-shaped hollow space, wherein the width of the slot extends along the longitudinal axis L. With such an arrangement, numerous idealized bending bars are formed from a mechanical perspective, which can bend and thus allow for a slight deformation, when the length L is extended.

The removal element 25 also has a blocking section 40, which is proximal to the engaging element 26 when the injection device is fully assembled. The engaging element 26 has an axial stop 42, which is in the form of a lug in the example shown in FIGS. 14 and 15, produced through deformation or stamping, for example, which extends outward, i.e. away from the longitudinal axis L. The axial stop 42 is flush with the blocking section 40 along the longitudinal axis L, e.g., radially aligned.

The blocking section 40 is connected via a connecting web, for example, to the coupling section 27 such that it cannot be displaced along the longitudinal axis L. There are two elongated connecting webs in the example, which connect the coupling section 27 to the blocking section 40. The blocking section 40 connects the two connecting webs at the circumference, wherein there is another blocking section 40 located on the opposite side that likewise connects the connecting webs at the circumference. The malleable section 28 is located along the circumference between the connecting webs. A substantially identical, further malleable section 28 is located opposite.

Figure 15:
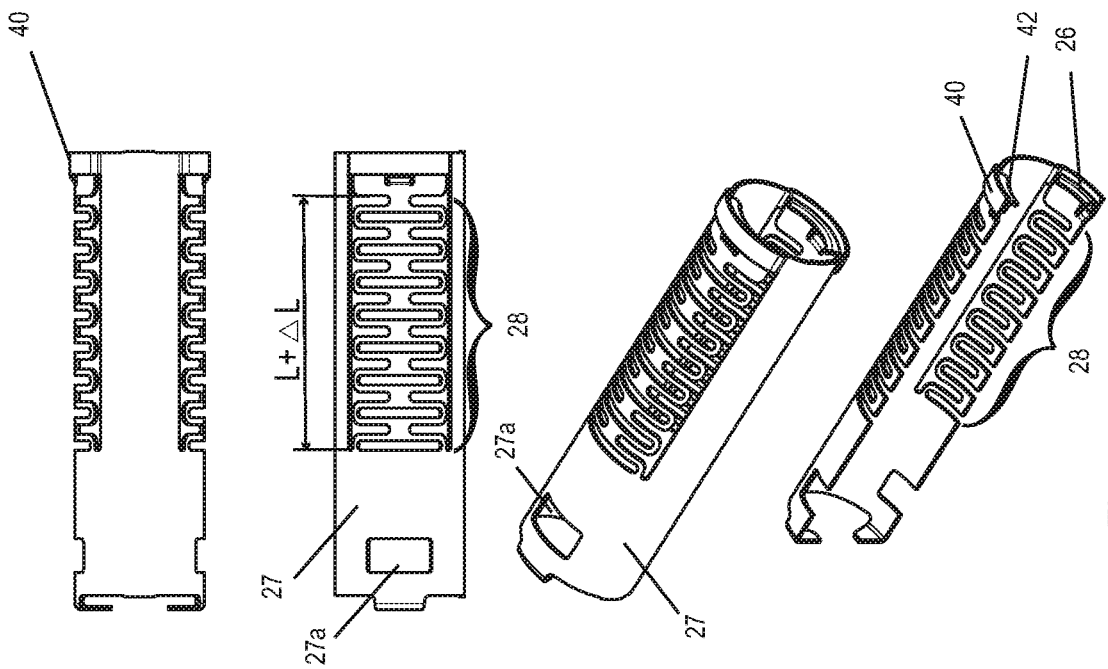
FIG. 15 shows the illustrations in FIG. 14, wherein a malleable section of the removal sleeve extends along the longitudinal axis, and a blocking section is pushed into a blocking position.
Figure 14:
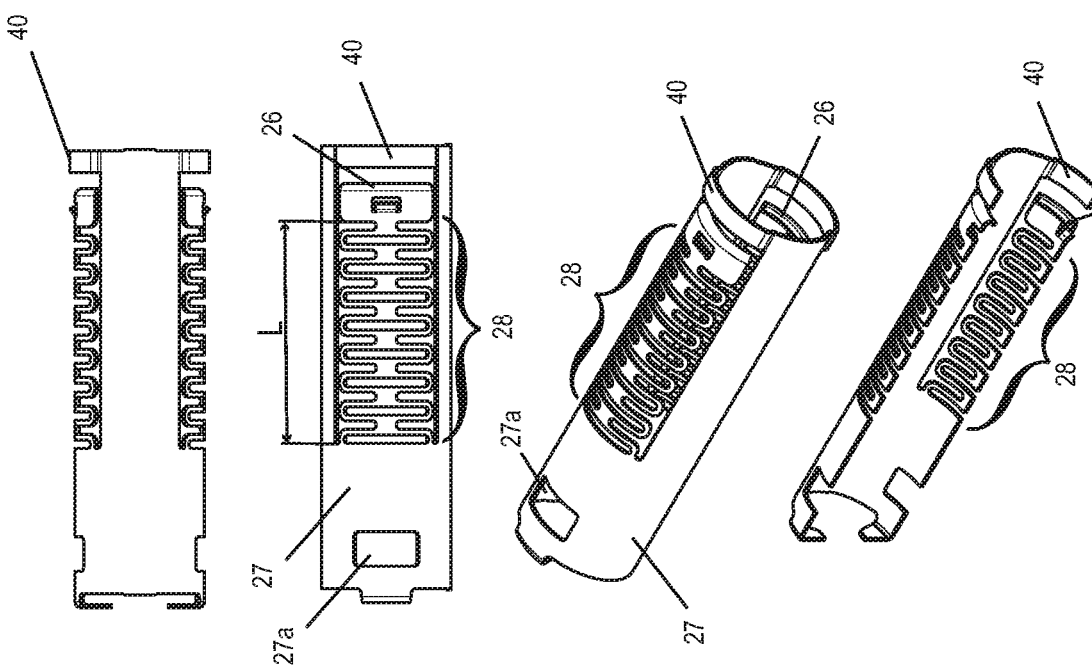

In order to remove the cap 20, it is released from the form fitting engagement with the receiving housing 1, and first moved distally as far as the first sub-movement h along the longitudinal axis. Because the coupling section 27 is axially secured to the cap 20, the coupling section 27 and the blocking section 40 connected non-displaceably thereto, are moved by the cap 20 during the first sub-movement, while the engaging element 26 remains stationary in relation to the receiving housing 1 or the product container 10, due to the engagement with the needle protection cap 17. As a result, the cap 20 and thus the coupling section 27 are moved distally in relation to the engaging element 26. At the same time, the blocking section 40 is moved from the releasing position into the blocking position (FIG. 15), wherein the blocking section 40 strikes the axial stop 42 in the blocking position. When in the blocking position, the blocking section 40 prevents an outward movement of the engaging element 26 transverse to the longitudinal axis L, i.e. away from the longitudinal axis. When the blocking section 40 moves from the releasing position into the blocking position, the malleable section 28 is lengthened by ΔL (FIGS. 15 and 17).

Because the blocking section 40 bears on the axial stop 42, the blocking section 40 carries the engaging element 26 distally along the longitudinal axis L in a further movement (second sub-movement), such that the needle protection cap 17 is moved, and is removed from the product container 10, in particular the needle retaining section 14 (FIG. 18).

In the second embodiment, the injection device comprises a sleeve-like removal element 25, which has a coupling section 27, which is connected to the cap 20 such that it cannot move axially, preferably such that it cannot rotate or move axially. The cap 20 has a projection 24 that engages in a recess 27a of the coupling section 27, such that the coupling section 27 cannot move along the longitudinal axis L in relation to the cap 20, and preferably cannot rotate about the longitudinal axis L. The inward projecting engaging element 26 is connected to the coupling section 27 via a malleable section 28. The malleable section 28 is configured such that it can extend along the longitudinal axis L, resulting in a lengthening of the length L by ΔL. The malleable section 28 becomes constricted as it lengthens (FIG. 9) such that its inner diameter is reduced, in particular in relation to the inner diameter when the malleable section 28 has its original length L (FIG. 8). The malleable section 28 has at least one spiral 31, 32, 33, which winds helically with at least one complete winding about the longitudinal axis L, and connects the coupling section 27 to a base section 43. The engaging element 26 is connected via an arm 29 to the base section 43, such that the engaging element 26 can move in a direction transverse to the longitudinal axis L, in particular in a spring-loaded manner. The malleable section 28 has numerous spirals 31, 32, 33 in the illustrated example, e.g. a first spiral 31, a second spiral 32, and a third spiral 33, which extend helically in at least one winding, and even more than two windings here, about the longitudinal axis L, and connects the coupling section 27 to the base section 43. Adjacent windings of the spirals 31, 32, 33 are connected by a connecting web. One or more, or all of these connecting webs have an engaging lobe 30, which extends inward from the inner circumference of the malleable section 28, in particular with a point of the engaging lobe 30 oriented in the distal direction.

The product container 10 is placed in the receiving housing 1 (FIGS. 10a, 10b) and displaced distally until it reaches its distal end position, such that the engaging element 26 is pushed into the gap 19, and assumes the engaging position.

In the fully assembled state, the injection device is in its engaging position (FIGS. 11a, 11b). In order to remove the cap 20, the form fitting engagement with the receiving housing 1 is first released, and the cap 20 is displaced distally over a distance or sub-movement x (FIGS. 12a, 12b), such that the coupling section 27 and the cap 20 are moved in relation to the engaging element 26, which is braced proximally at the proximal end of the needle protection cap 17. As a result, the malleable section is extended by ΔL (FIG. 9), resulting in a constriction of the malleable section 28 such that the engaging lobes 30 grip the outer circumference or outer surface of the needle protection cap 17, as a result of which, the force exerted on the cap 20 in the distal direction is not only transferred to the needle protection cap 17 via the engaging element 26, but also via the engaging lobes 30 engaged in the needle protection cap 17. If the cap 20 is then moved further distally, the engagement of the needle protection cap 17 with the product container, in particular the needle retaining section 14 is released, such that the needle protection cap 17 is removed, together with the cap 20, from the injection device (FIGS. 13a, 13b).

The assembly procedure, in particular the integration of the product container 10 in the receiving housing 1 of the injection device, is substantially similar in the three embodiments shown in the drawings. The product container 10, to which the needle protection cap 17 is already attached before it is placed in the receiving housing 1 in order to keep the injection needle 11 sterile, is inserted, with the needle protection cap 17 on it, into the receiving housing 1 through an opening at the proximal end of the receiving housing 1, along the longitudinal axis L in the distal direction. In particular, the product container 10 is inserted thereby into the product container retainer 2 supported in the receiving housing 1. The product container retainer 2, which can be displaced in relation to the receiving housing 1 in these examples, bears on the cap in order to block its movement along the longitudinal axis L during the assembly, such that a distal displacement of the product container retainer 2 is prevented when the cap 20 is attached to the receiving housing 1. When the product container 10 is inserted into the receiving housing 1, the engaging element 26 slides along needle protection cap 17 and is pressed radially outward by the needle protection cap 17, in particular its outer surface. This is possible in particular in the first and third embodiments because the blocking section 40 is in its releasing position, and not in its blocking position (FIGS. 4a, 4b, 16a, 16b). In the second embodiment, although there is no blocking section 40, the engagement of the removal element 25 with the needle protection cap 17 is reinforced by the constriction of the malleable section 28 when the cap 20 is removed. When the product container 10 has been fully inserted into the receiving housing 1, the engaging element 26 snaps into its engaging position between the tapered end of the product container section 2 and the proximal end of the needle protection cap 17. The drive housing 5 is subsequently joined or connected to the receiving housing 1, such that the injection device is fully assembled.

Because there is a malleable section 28 that becomes constricted when the cap 20 is removed in the second embodiment, and is displaced in relation to the engaging element, either through a sub-movement or deformation, and transfers a least part of the removal force applied to the cap 20 to the needle protection cap 17 as a result, the respective engaging elements 26 can be located on the removal element 25 in all of the embodiments, such that it can be moved or pivoted outward, i.e. in a basically radial direction away from the longitudinal axis L, with relatively little force. As a result, the danger of the needle protection cap 17 being removed from the engaging element on the needle retaining section 14 of the product container 10 is reduced, e.g. as would otherwise be the case if the engaging element were too big. A movement of the needle protection cap 17 on the needle retaining section 14 can endanger the sterility of the injection needle 11.

An auto-injector shall be described below, which can be used with a removable cap, preferably but not necessarily a removable cap of the type described above.

Figure 19:
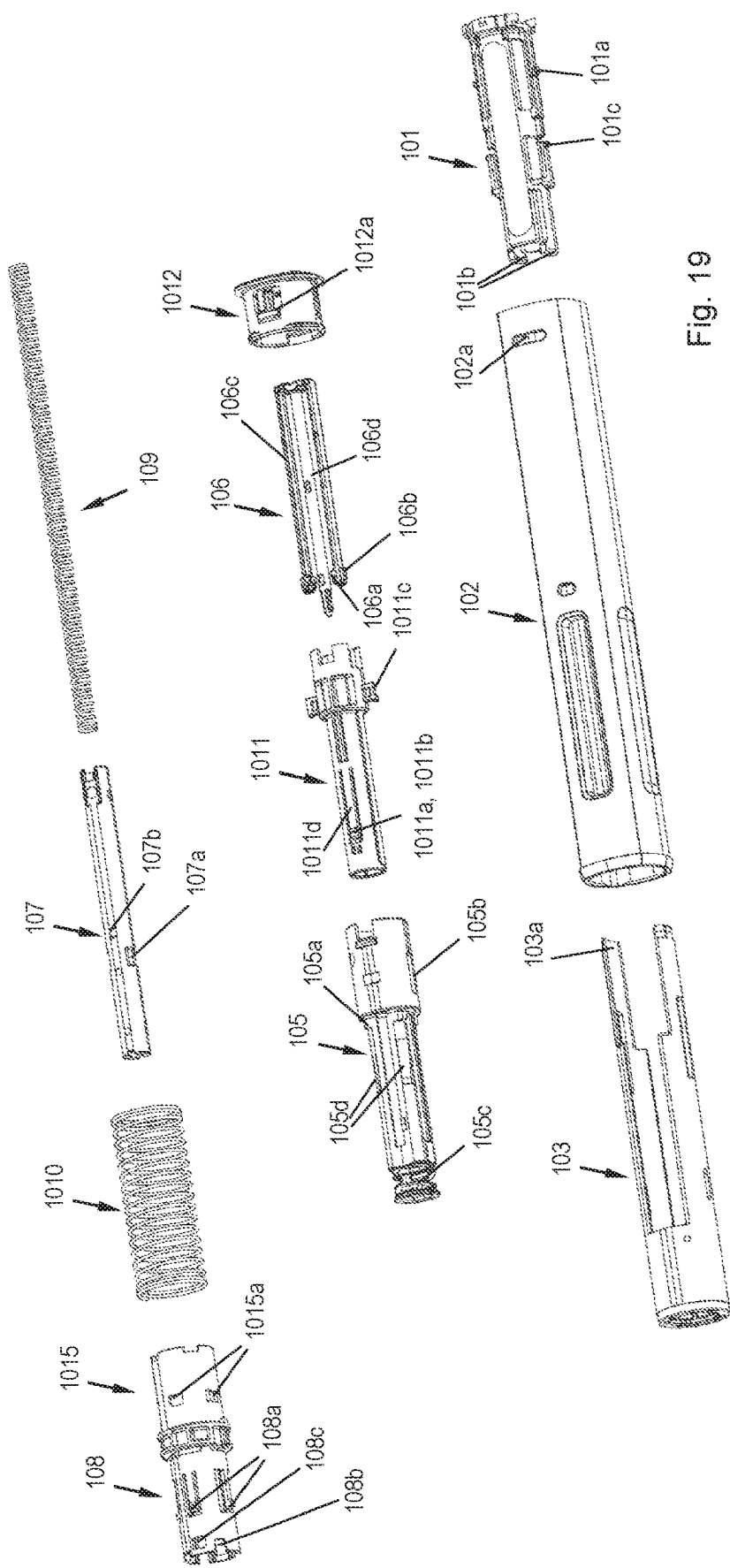
FIG. 19 shows an exploded view of an auto-injector.

The auto-injector (FIG. 19) has a sleeve-like, elongated housing 102 that has a longitudinal axis L, which has a sealing cap 1012 on its proximal end, which is connected in a form fitting manner to the housing 102 such that it cannot rotate or move axially, and forms the proximal end of the auto-injector. The sealing cap 1012 is snapped onto the housing 102. For this, the sealing cap 1012 has a catch 1012a, which snaps into a recess 102a on the housing 102, preferably such that the sealing cap 1012 cannot be released, or easily released, from the housing 102.

In its delivery state, a needle protection cap 20 (not shown in FIG. 19) of the type described above can be located at the distal end of the auto-injector, which can be pulled or twisted off of the auto-injector before use, and is removed.

A product container in the form of a syringe is received in the housing 102 such that—aside from in the assembly of the auto-injector—it cannot be displaced along the longitudinal axis L. The product container has a sleeve-like syringe element, which encompasses a piston that bears in a sealing manner on the inner circumference of the syringe element. The syringe element has an injection needle at its distal end, which is permanently connected to the syringe element, the distal end of which is formed by the tip of the needle. A liquid product, in particular a medicine, is located in the syringe element between the injection needle and the piston, wherein the liquid product is dispensed by displacing the piston in a dispensing direction, i.e. in a distal direction, or toward the injection needle, such that the product is dispensed through the hollow injection needle. The syringe element has a so-called finger-flange at its proximal end, which extends radially outward, over the outer circumference of the cylindrical syringe element.

The product container is received in a product container retainer, referred to as a syringe retainer 101, such that it is secured against movement along the longitudinal axis L in the distal direction in relation to the syringe retainer 101. The syringe retainer 101 is connected in a form fitting manner to the housing 102, in particular such that it is snapped thereon. The housing 102 has recesses for this, in which the snap-in elements, formed at the proximal end of the syringe retainer 101, engage. The syringe retainer 101 has at least one shoulder 101b that extends inward, on which a tapered section of the product container is supported.

In order to prevent the product container from being able to be displaced proximally in relation to the syringe retainer 101, the product container is pressed into engagement with the shoulder 101b by a retainer acting on the syringe element. The retainer is formed by a retaining spring section 105c of a mechanical retainer 105. The mechanical retainer 105 cannot be displaced and/or is non-rotatable in relation to the housing 102 along the longitudinal axis L. The sleeve-like mechanical retainer 105 can be snapped onto the housing 102. Differences in the lengths of product containers resulting from production tolerances can be compensated for by the retaining spring section 105c, wherein it is ensured that the product container is securely seated on the shoulder 101b.

The product container is located in relation to the housing 102 such that the tip of the needle extends distally beyond the distal end of the housing 102. In the initial or delivery state of the auto-injector, i.e. when the removable cap 20 is on the auto-injector, the needle is covered by a needle cover cap 17, which is in the form of a rigid needle shield or a soft needle shield in the illustrated examples, and known to the person skilled in the art, in order to protect the needle from contamination, and to keep the needle and the medicine sterile. The rigid needle shield is located on a needle retaining section of the syringe element, wherein the tapered section of the syringe element is located between the needle retaining section and the cylindrical section of the syringe element. The shoulder 101b is located between the syringe element and the proximal end of the rigid needle shield, in particular such that there is a—slightly smaller—gap between the rigid needle shield and the shoulder 101b, to prevent the shoulder 101b from exerting a force on the rigid needle shield that could endanger, e.g., the sterility of the needle or the liquid product. The removable cap 20 is snapped onto the housing 102 or a needle protection sleeve 103, such that it can be released therefrom, wherein this snap-on connection is released when the removable cap 20 is removed from the housing 102 or the needle protection sleeve 103.

The auto-injector has a needle protection sleeve 103, which can be displaced in relation to the housing 102 and along the longitudinal axis L as far as an actuation movement $H_B$ in the proximal direction, into an actuated position, in order to trigger a dispensing of the product. The distal end of the needle protection sleeve 103 extends distally beyond the tip of the needle in the initial position, such that access to the tip of the needle is initially prevented. By displacing the needle protection sleeve 103 the length of the actuation movement $H_B$, the needle protection sleeve 103 is displaced proximally until the needle extends out of the distal end of the needle protection sleeve 103, in particular at a length corresponding to the depth of the injection of the needle into the injection site. The needle should preferably extend far enough beyond the distal end of the needle protection sleeve 103 that a subcutaneous injection can take place. In particular, the housing 103 can form a stop, against which the needle protection sleeve 103 bears when in the actuated position.

After the injection, the needle protection sleeve 103 can be moved distally in relation to the housing 102, from the actuated position by a needle protection movement $H_N$ along the longitudinal axis L into a needle protecting position. In the needle protecting position, the distal end of the needle protection sleeve 103 extends distally beyond the tip of the needle, such that access to the tip of the needle is prevented, and the risk of injury is reduced. The needle protection sleeve 103 can be blocked against a renewed return displacement from the needle protecting position.

The syringe retainer 101 has a projection 101a, which faces radially outward, wherein the projection 101a engages in a slot-shaped recess in the needle protection sleeve 103, located between the housing 102 and the syringe retainer 101. When the needle protection sleeve 103 is in the initial position and/or in the needle protecting position, the needle protection sleeve 103, in particular the proximal end of the slot-shaped recess, bears on the projection 101a, such that movement of the needle protection sleeve 103 in the distal direction is prevented. A lobe 101c, supported in a spring-loaded manner on the syringe retainer 101 and formed by the syringe retainer 101, can engage in this slot-shaped recess, or in another recess in the needle protection sleeve 103. The lobe 101c is configured such that when attempting to displace the needle protection sleeve 103 from the initial position to the actuated position, the lobe 101c initially prevents the displacement of the needle protection sleeve 103, wherein the lobe 101c is pressed out of the recess when the force applied to the needle protection sleeve 103 for pushing it back exceeds a certain threshold value, such that the needle protection sleeve 103 is abruptly pushed back into the actuated position. As a result, the needle can be abruptly inserted into the injection site. In order to insert the needle, or to displace the needle protection sleeve 103 into the actuated position, the distal end of the needle protection sleeve 103 is placed in the injection site, wherein the housing 102 is then pushed toward the injection site, wherein, when the pressure exceeds the aforementioned threshold value, the housing 102 is abruptly pushed toward the injection site, and the needle protection sleeve 103 is pushed into the actuated position in relation to the housing 102.

The housing 102 has an annular retaining section, which encompasses the distal end of the syringe retainer 102, in particular in an annular manner, and bears thereon, such that the at least one shoulder 101 is retained in engagement with the tapered region of the syringe element. Furthermore, the housing 102 has a translation stop in the region of the retaining section in the form of a retaining shoulder, which prevents distal displacement of the syringe retainer 101 in relation to the housing 102, when the syringe retainer 1 bears on the retaining shoulder. This also applies advantageously to the variations described herein.

The auto-injector also has a sleeve-like propulsion element 107, which forms a shoulder that projects inward at its distal end, on which a first spring 109, which can also be referred to as a dispensing shoulder, bears. The first spring 109 is located inside the sleeve-like propulsion element 107. The second spring 109 is a helical spring, acting as a compression spring, which is pretensioned in the initial or delivery state, such that it can dispense the product contained in the product container, in particular entirely, by displacing the propulsion element 107 the length of a dispensing movement $H_A$ from the product container. In the delivery state of the device, there is a spacing between the piston and the distal end of the propulsion element 107, such that the propulsion element 107 first strikes the piston during the execution of the dispensing movement $H_A$, and pushes it along in the dispensing direction.

The first spring 109 bears at its proximal end on a retaining element 106, which has two arms 106c in this example, wherein a first engaging element 106a and a second engaging element 106b are located on each arm 106c. The first engaging element 106a faces the longitudinal axis L radially, while the second engaging element 106b faces radially away from the longitudinal axis L. The first engaging element 106a engages in a first recess 107a, formed by the propulsion element 107, such that a distal movement of the propulsion element 107 in relation to the retaining element 106, or in the dispensing direction, is prevented. As a result, the first spring 109 is retained in its tensioned state. The retaining element 106 has a guide pin 106d, which is inserted into the core of the spring 109 through the proximal end of the first spring 109. The guide pin 106d prevents a lateral buckling of the first spring 109 during and at the end of the dispensing movement $H_A$ of the propulsion element 107.

The auto-injector has a switching module 108, 1015, which has a switching sleeve 1015 and a blocking sleeve 108 encompassed by the switching sleeve 1015. In the delivery state of the device, the first engaging element 106a is retained by the inner circumference of the blocking sleeve 108, which bears on the second engaging element 106b, in the engagement with the first recess 107a.

The switching sleeve 1015 is connected to the proximal end 103a of the needle protection sleeve 103, or bears at least on the proximal end 103a of the needle protection sleeve 103. A second spring 1010, within which the first spring 109 is located, and which preferably at least partially encompasses the switching sleeve 1015 and the blocking sleeve 108, bears at its distal end on the switching sleeve 1015. A part of the switching sleeve 1015 is thus located between the needle protection sleeve 103 and the distal end of the second spring 1010. The second spring 1010 is a compression spring made of metal in the form of a helical spring. The second spring 1010 bears at its proximal end on a signal element 1011, in particular a projection 1011c, which engages in the housing 102, such that it can be displaced axially, and cannot rotate, and which passes through a slot-shaped groove 105b in the mechanical retainer 105. The second spring 101 thus encompasses the mechanical retainer 105 as well, at least in part, preferably entirely.

The switching element 1015 has a recess 1015a, in which a locking element 108a of the locking sleeve 108 engages. The locking element 108a is serrated, and extends radially away from the longitudinal axis L. The locking element 108a is supported in a spring-loaded manner on an arm formed by the blocking sleeve 108. By displacing the switching sleeve 1015 in the proximal direction, the locking sleeve 108 is moved proximally via the engagement of the locking element 108a.

By displacing the needle protection sleeve 103 into the actuated position, the switching sleeve 1015 is likewise moved the length of the actuating movement $H_B$, such that the second spring 1010 is tensioned. If the needle protection sleeve 103 is not pushed all the way into the actuated position, the second spring 1010 can push the switching sleeve 1015 and the needle protection sleeve 103 back into the starting position, wherein the blocking sleeve 108 is also moved by the switching sleeve 1015 via the engagement of the locking element 108a.

The sleeve-like signal element 1011 is engaged with the propulsion element 107 in an axially fixed manner in the delivery state or prior to triggering the dispensing of the product. The signal element 1011 has a first engaging element 1011a, which engages in a recess 107b in the propulsion element 107, and a second engaging element 1011b. The first engaging element 1011a and the second engaging element 1011b are located on the end of an arm 1011d, supported in a spring-loaded manner. The signal element 1011 has two such arms 1011d, which have a first engaging element 1011a and a second engaging element 1011b. The first engaging element 1011a faces radially toward the longitudinal axis L, and the second engaging element 1011b faces radially away from the longitudinal axis L. In the delivery state, the first engaging element 1011a is retained in the axially fixed engagement with the propulsion element 107 by the inner circumference of the blocking sleeve 108. The second engaging element 1011b bears on the inner circumference of the switching sleeve 108. The sealing cap 1012 has a signal stop 12b, which the signal element 1011 can strike in order to generate a signal, and which preferably bears on the signal element 1011 in the delivery state of the device.

In order to administer the product from the product container, the removable cap 20, together with the rigid needle shield, is removed from the auto-injector. The distal end of the needle protection sleeve 103 is placed at the injection site on a patient, wherein the housing 102 is displaced toward the injection site, such that the needle protection sleeve 103 is moved proximally in relation to the housing 102, from its initial position to the actuated position by the actuation movement $H_B$. As a result, the second spring 1010 is tensioned, wherein the switching sleeve 1015 is moved away from the needle protection sleeve 103 as far as the actuation movement $H_B$. The blocking sleeve 108 has a first recess 108b, which is brought to the position of the second engaging element 106b by displacing the blocking sleeve 108 as far as the actuation movement $H_B$ along the longitudinal axis L. As a result, the first engaging element 106a is disengaged from the propulsion element 107 with a movement transverse to and away from the longitudinal axis L, wherein the second engaging element 106b becomes engaged with the blocking sleeve 108 at the same time, in particular at its first recess 108b. As a result, the propulsion element 107 is allowed to move in the dispensing direction as far as the dispensing movement $H_A$.

Because the axially fixed coupling between the propulsion element 107 and the retaining element 106 is now released, the retaining element 106, which can move at least a little in relation to the housing 102 and along the longitudinal axis L, is moved by the first spring 109 in the proximal direction, wherein the retaining element 106 moves the blocking sleeve 108 as far as a starting signal movement HK via the engagement of the second engaging element 106b in the recess 108b, such that the blocking sleeve 108 strikes a starting signal stop 105a, formed by the mechanical retainer 105, and thus emits an acoustic and/or tactile signal, which indicates to the user of the device that the product dispensing has begun. By displacing the blocking sleeve 108 as far as the actuation movement $H_B$, the locking element 108a is allowed to move in a transverse direction and toward the longitudinal axis L, because the mechanical retainer 105 has an indentation 105d, which allows for such a movement of the locking element 108a, when the blocking sleeve 108 is displaced as far as the actuating movement $H_B$, or when the needle protection sleeve 103 is in its actuated position.

Because the signal element 1011 is still connected to the propulsion element 107 in an axially fixed manner, it is moved a first sub-movement $H_S$ of the dispensing movement $H_A$ in the dispensing direction, wherein the signal element 1011 is moved away from the signal stop 1012B as far as the first sub-movement $H_S$. At the end of the first sub-movement $H_S$, during which the first and second engaging elements 1011a, 1011b are moved in relation to the blocking sleeve 108, the first engaging element 1011a is disengaged from the propulsion element 107, wherein the second engaging element 1011b is moved at the same time into the second recess 108c of the blocking sleeve 108 with a movement transverse to the longitudinal axis L and radially away from the longitudinal axis L. As a result, the signal element 1011 is prevented from moving proximally in relation to the housing 102 or the blocking sleeve 108. The second engaging element 1011b is kept in engagement with the recess 108c by the outer circumference of the propulsion element 107 when the propulsion element 107 is moved a second sub-movement of the dispensing movement $H_A$. The outer circumference of the propulsion element 107 keeps the second engaging element 106b in engagement with the first recess 108b of the blocking sleeve 108. At the end of the dispensing movement $H_A$, the propulsion element 107 releases the second engaging element 1011b from the engagement with the blocking sleeve 108, such that the second engaging element 1011b is disengaged from the recess 108c, in particular toward the longitudinal axis L, such that the second spring 1010 accelerates the signal element 1011 counter to the dispensing direction, i.e. in the proximal direction, such that when the signal element 1011 strikes the signal stop 1012b, and acoustic and/or tactile signal is generated.

The engagement of the second engaging element 106b in the first recess 108b remains intact, such that a distal movement of the blocking sleeve 108 in relation to the housing 102 is prevented.

By removing the auto-injector from the injection site, the second spring 1010 can move the switching sleeve 1015 and the needle protection sleeve 103 from the actuated position into the needle protecting position as far as the needle protecting movement $H_N$, wherein the locking element 108a is disengaged from the recess 1015*a*, wherein the switching sleeve 1015 is moved distally in relation to the blocking sleeve 108. When the needle protection sleeve 103 is in its needle protecting position, the locking element 108*a* is snapped onto the switching sleeve 1015, wherein the locking element 108*a* prevents a return displacement of the needle protection sleeve 103 to its actuated position. When it is attempted to move the needle protection sleeve 1033 from the needle protecting position back to its actuated position, the switching element 1015 strikes the locking element 108*a*, preventing the movement of the needle protection sleeve 103 back into the actuated position. The blocking sleeve 108 bears axially on the starting signal stop 105*a* of the mechanical retainer 105 for this.

LIST OF REFERENCE SYMBOLS FIGS. 1-18

1 receiving housing
2 product container retainer
3 needle protection sleeve
4 spring
5 drive housing
10 product container
11 injection needle
12 product container section
13 piston
14 needle retaining section
15 product
16 flange
17 needle protection cap
18 circumference/outer surface
19 gap
20 cap
21 sleeve section
22 engaging element
23 inner sleeve
24 projection
25 removal element
26 engaging element
27 coupling section
27*a* recess
28 malleable section
29 arm
30 engaging lobe
31 first spiral
32 second spiral
33 third spiral
34 connecting web
40 blocking section
41 releasing section/recess
42 axial stop
43 base section
L longitudinal axis

What is claimed is:

1. An injection device, comprising:
   a product container comprising an injection needle, wherein the product container has a tapered distal end;
   a needle protection cap, releasably connected to the product container, and encompassing the injection needle and sealing it in a sterile manner, wherein a gap is formed between the tapered distal end of the product container and a proximal end of the needle protection cap;
   a cap coupled to the needle protection cap via a removal element, the removal element comprising an engaging element, wherein removal of the cap from the injection device results in removal of the needle protection cap from the product container; and
   a blocking section coupled to the cap and arranged proximally to the proximal end of the needle protection cap,
   wherein the engaging element is in an engaging position in relation to the needle protection cap when the engaging element is arranged in the gap and a section of the needle protection cap is axially aligned with the engaging element relative to a longitudinal axis (L) of the injection device,
   wherein the cap and the engaging element are coupled such that the cap can be or is moved in relation to the engaging element during removal of the cap from the injection device when the engaging element is in the engaging position,
   wherein the blocking section is movable from a releasing position to a blocking position, wherein the blocking section is in the releasing position when the cap is entirely placed on or attached to a receiving housing such that the blocking section does not block a transverse, outward movement of the engaging element, and wherein the blocking section is moved to the blocking position during removal of the cap such that the blocking section blocks movement of the engaging element out of the engaging position.

2. The injection device according to claim 1, wherein the cap can be or is first moved in relation to the engaging element during removal of the cap from the injection device, and wherein the engaging element subsequently moves with the cap, by means of which the needle protection cap is removed from or pulled off of the product container.

3. The injection device according to claim 1, wherein the cap can be removed from the injection device with an axial movement or a combined axial-rotational movement.

4. The injection device according to claim 1, wherein the cap is releasably connected to a receiving housing, which encompasses the product container.

5. The injection device according claim 1, wherein the blocking section is formed by the cap, wherein the cap comprises a recess located in a position along the longitudinal axis (L) at a height of the engaging element when the blocking section is in the releasing position, wherein the blocking section is moved to the blocking position by removing the cap.

6. The injection device according to claim 1, wherein the blocking section is formed by the removal element, wherein the blocking section and the engaging element are coupled via a malleable section, which becomes deformed when the blocking section is moved from the releasing position to the blocking position.

7. A method for assembling and/or for preparing an injection device for administering a product, comprising the following steps:
   providing a receiving housing for receiving a product container, wherein a cap is placed on a distal end of the receiving housing, wherein a removal element is located in the cap, and the removal element comprises an engaging element that can move in a direction transverse to a longitudinal axis (L) of the receiving housing, and wherein a blocking section is coupled to the cap;
   providing a product container comprising a product container section and an injection needle connected to the product container section, wherein the product container section comprises a displaceable piston, wherein the product is located between the injection needle and the piston, wherein a needle protection cap is located on the product container, which encompasses the needle and seals it in a sterile manner, wherein a gap is formed between a distal end of the product container and a proximal end of the needle protection cap;

sliding the product container along with the needle protection cap attached thereto into the receiving housing, distally along the longitudinal axis (L), wherein the engaging element is deflected from an outer surface of the needle protection cap when the product container is slid, together with the needle protection cap, and the outer surface of the needle protection cap slides along the engaging element, wherein the engaging element is moved or pushed by a spring force into a position at an end of the displacement of the product container by a movement transverse to the longitudinal axis (L), wherein the engaging element is arranged in the gap, a section of the needle protection cap is axially aligned with the engaging element when in an engaging position relative to the longitudinal axis (L), and wherein the blocking section does not block a transverse, outward movement of the engaging element and such that that the cap is entirely placed on or attached to the receiving housing and the blocking section is arranged proximally to the proximal end of the needle protection cap in a releasing position of the blocking section; and removing the cap from the receiving housing, wherein the cap and the engaging element are coupled such that the cap is moved in relation to the engaging element during removal of the cap from the injection device and the engaging element is in the engaging position, and as the cap is removed, the blocking section moves to a blocking position in which the blocking section blocks movement of the engaging element out of the engaging position.

8. The method according to claim 7, wherein the engaging element is moved into the engaging position at the end of the displacement of the product container by the movement transverse to the longitudinal axis (L).

9. The method according to claim 7, wherein the blocking section is formed by the cap, wherein the cap comprises a recess at a height of the engaging element along the longitudinal axis (L) when the blocking section is in the releasing position, wherein the blocking section is moved into the blocking position by removing the cap.

10. The method according claim 7, wherein the blocking section is formed by the removal element, wherein the blocking section and the engaging element are coupled via a malleable section, which is deformed when the blocking section is moved from the releasing position to the blocking position.

* * * * *